United States Patent
Hewitt et al.

(10) Patent No.: US 12,163,146 B2
(45) Date of Patent: Dec. 10, 2024

(54) QUALITY CONTROL METHODS FOR AUTOMATED CELL PROCESSING

(71) Applicant: LONZA WALKERSVILLE, INC., Walkersville, MD (US)

(72) Inventors: Matthew Hewitt, Walkersville, MD (US); Eytan Abraham, Walkersville, MD (US); Nicholas Ostrout, Walkersville, MD (US)

(73) Assignee: LONZA WALKERSVILLE, INC., Walkersville, MD (US)

( * ) Notice: Subject to any disclaimer, the term of this patent is extended or adjusted under 35 U.S.C. 154(b) by 362 days.

(21) Appl. No.: 17/093,943

(22) Filed: Nov. 10, 2020

(65) Prior Publication Data

US 2021/0148895 A1    May 20, 2021

Related U.S. Application Data

(60) Provisional application No. 62/933,575, filed on Nov. 11, 2019.

(51) Int. Cl.
   *C12N 15/85* (2006.01)
   *C12N 5/0783* (2010.01)

(52) U.S. Cl.
   CPC .......... *C12N 15/85* (2013.01); *C12N 5/0636* (2013.01); *C12N 2501/51* (2013.01); *C12N 2501/515* (2013.01); *C12N 2502/1121* (2013.01); *C12N 2502/1157* (2013.01)

(58) Field of Classification Search
   None
   See application file for complete search history.

(56) References Cited

U.S. PATENT DOCUMENTS

| | | |
|---|---|---|
| 4,642,120 A | 2/1987 | Nevo et al. |
| 4,939,151 A | 7/1990 | Bacehowski et al. |
| 5,041,138 A | 8/1991 | Vacanti et al. |
| 5,081,036 A | 1/1992 | Familletti |
| 5,240,854 A | 8/1993 | Berry et al. |
| 5,246,699 A | 9/1993 | Debre et al. |
| 5,424,209 A | 6/1995 | Kearney |
| 5,478,479 A | 12/1995 | Herrig |
| 5,549,134 A | 8/1996 | Browne et al. |
| 5,688,687 A | 11/1997 | Palsson et al. |
| 5,728,581 A | 3/1998 | Schwartz et al. |
| 5,786,207 A | 7/1998 | Katz et al. |
| 5,792,603 A | 8/1998 | Dunkelman et al. |
| 5,827,729 A | 10/1998 | Naughton et al. |
| 5,842,477 A | 12/1998 | Naughton et al. |
| 5,846,828 A | 12/1998 | Peterson et al. |
| 5,882,929 A | 3/1999 | Fofonoff et al. |
| 5,891,455 A | 4/1999 | Sittinger et al. |
| 5,902,741 A | 5/1999 | Purchio et al. |
| 5,906,934 A | 5/1999 | Grande et al. |
| 5,922,604 A | 7/1999 | Stapleton et al. |
| 5,928,936 A | 7/1999 | Ingram |
| 5,985,653 A | 11/1999 | Armstong et al. |
| 5,989,913 A | 11/1999 | Anderson et al. |
| 5,994,129 A | 11/1999 | Armstrong et al. |
| 6,048,721 A | 4/2000 | Armstrong et al. |
| 6,048,722 A | 4/2000 | Farb et al. |
| 6,060,306 A | 5/2000 | Flatt et al. |
| 6,096,532 A | 8/2000 | Armstrong et al. |
| 6,121,042 A | 9/2000 | Peterson et al. |
| 6,123,655 A | 9/2000 | Fell |
| 6,197,575 B1 | 3/2001 | Griffith et al. |
| 6,214,574 B1 | 4/2001 | Kopf |
| 6,228,635 B1 | 5/2001 | Armstrong et al. |
| 6,238,908 B1 | 5/2001 | Armstrong et al. |
| 6,297,046 B1 | 10/2001 | Smith et al. |
| 6,323,146 B1 | 11/2001 | Pugh et al. |
| 6,402,941 B1 | 6/2002 | Lucido et al. |
| 7,348,175 B2 | 5/2008 | Vilendrer et al. |
| 7,906,323 B2 | 3/2011 | Cannon et al. |
| 9,629,877 B2 | 4/2017 | Cooper et al. |
| 10,131,876 B2 * | 11/2018 | Kaiser ................. C12N 5/0087 |
| 10,253,316 B2 | 4/2019 | Masquelier et al. |
| 10,273,300 B2 | 4/2019 | Bedoya et al. |
| 11,208,626 B2 | 12/2021 | Mason et al. |
| 11,447,745 B2 * | 9/2022 | Shi ......................... C12M 41/48 |

(Continued)

FOREIGN PATENT DOCUMENTS

| | | |
|---|---|---|
| AU | 2002/324169 A1 | 3/2003 |
| DE | 4021123 A1 | 4/1991 |

(Continued)

OTHER PUBLICATIONS

Jakubzick et al. Monocyte differentiation and antigen-presenting functions. Nat Rev Immunol. Apr. 2017; 17: 349-362. (Year: 2017).*

Fraietta et al. Determinants of response and resistance to CD19 chimeric antigen receptor (CAR) T cell therapy of chronic lymphocytic leukemia. Nat Med. May 2018; 24(5): 563-571. (Year: 2018).*

Thomas, RJ et al., Cell Culture Automation and Quality Engineering: A Necessary Partnership to Develop Optimized Manufacturing Processes for Cell-Based Therapies, Journal of the Association for Laboratory Automation, Jun. 2008, vol. 13, No. 3; pp. 152-158; p. 154, 1st column 4th paragraph to 2nd column 4th paragraph; p. 155, 1st column 2nd paragraph to 2nd column 2nd paragraph; p. 156, 1st column 2nd paragraph; DOI: 10.1016/j.jala.2007.12.003.

(Continued)

*Primary Examiner* — Allison M Fox
*Assistant Examiner* — Alyssa G Weston
(74) *Attorney, Agent, or Firm* — MEDLER FERRO WOODHOUSE & MILLS PLLC

(57) ABSTRACT

The present disclosure provides methods for assessing and optimizing cellular quality of a cell-based therapy that is being produced in an automated cell engineering system. The methods suitably include monitoring molecular characteristics of the cells before, during, and after the automated process to provide feedback to the process parameters. In embodiments, the cells being produced are Chimeric Antigen Receptor (CAR) T-cells.

23 Claims, 5 Drawing Sheets

(56) References Cited

U.S. PATENT DOCUMENTS

| | | |
|---|---|---|
| 2001/0021529 A1 | 9/2001 | Takagi |
| 2001/0043918 A1 | 11/2001 | Masini et al. |
| 2002/0009797 A1 | 1/2002 | Wolf et al. |
| 2002/0009803 A1 | 1/2002 | Gabor Vajta |
| 2002/0025547 A1 | 2/2002 | Rao |
| 2002/0037580 A1 | 3/2002 | Schoeb |
| 2002/0146816 A1 | 10/2002 | Vellinger et al. |
| 2002/0155487 A1 | 10/2002 | Greenberger et al. |
| 2002/0179525 A1 | 12/2002 | Shaffer et al. |
| 2003/0032071 A1 | 2/2003 | Wang et al. |
| 2003/0040104 A1 | 2/2003 | Barbera-Guillem |
| 2003/0054335 A1 | 3/2003 | Taya et al. |
| 2003/0159946 A1 | 8/2003 | Eden et al. |
| 2003/0215935 A1 | 11/2003 | Coon |
| 2004/0048364 A1 | 3/2004 | Trosch |
| 2005/0064465 A1 | 3/2005 | Dettloff et al. |
| 2005/0130297 A1 | 6/2005 | Sarem et al. |
| 2005/0186671 A1 | 8/2005 | Cannon et al. |
| 2015/0344844 A1 | 12/2015 | Better et al. |
| 2016/0122782 A1 | 5/2016 | Crisman et al. |
| 2017/0037369 A1 | 2/2017 | Ramsborg et al. |
| 2017/0051252 A1 | 2/2017 | Morgan et al. |
| 2019/0002814 A1* | 1/2019 | Masquelier ............ C12N 15/11 |
| 2019/0211294 A1 | 7/2019 | Karnieli |
| 2020/0066369 A1 | 2/2020 | Downey |

FOREIGN PATENT DOCUMENTS

| | | |
|---|---|---|
| EP | 0248675 A1 | 12/1987 |
| GB | 1356794 A | 6/1974 |
| JP | 2-119772 A | 5/1990 |
| JP | 2-174848 A | 7/1990 |
| JP | 3-500847 A | 2/1991 |
| JP | 5-503418 A | 6/1993 |
| JP | 6-54678 A | 3/1994 |
| JP | 6-261736 A | 9/1994 |
| JP | 7-501206 A | 2/1995 |
| JP | H08-56646 A | 3/1996 |
| JP | H11-507229 A | 6/1999 |
| JP | 2001-275659 A | 10/2001 |
| JP | 2001-517428 A | 10/2001 |
| JP | 2002-500004 A | 1/2002 |
| KR | 20000023786 U | 9/2001 |
| WO | 91/05849 A1 | 5/1991 |
| WO | 93/03142 A1 | 2/1993 |
| WO | 1997/12960 A2 | 4/1997 |
| WO | 99/33951 A1 | 7/1999 |
| WO | 99/47922 A2 | 9/1999 |
| WO | 2000/046349 A1 | 8/2000 |
| WO | 01/02030 A2 | 1/2001 |
| WO | 2001/000783 A2 | 1/2001 |
| WO | 2002/028996 A1 | 4/2002 |
| WO | 02/088295 A1 | 11/2002 |
| WO | 03/022985 A2 | 3/2003 |
| WO | 03/087292 A2 | 10/2003 |
| WO | 2003/085101 A1 | 10/2003 |
| WO | 2015/162211 A1 | 10/2015 |
| WO | 2016/069993 A1 | 5/2016 |
| WO | 2016/118780 A1 | 7/2016 |
| WO | 2016/168275 A1 | 10/2016 |
| WO | 2017/068425 A1 | 4/2017 |
| WO | 2018/015561 A1 | 1/2018 |
| WO | 2019046766 A2 | 3/2018 |
| WO | 2018/136566 A1 | 7/2018 |
| WO | 2018232265 A1 | 12/2018 |

OTHER PUBLICATIONS

Pandey, PR et al., End-to-End Platform for Human Pluripotent Stem Cell Manufacturing, International Journal of Molecular Sciences. Jan. 2020, Epub Dec. 21, 2019, vol. 21, No. 1; pp. 1-29; DOI: 10.3390/ijms21010089.

Konstantin B. Konstantinov "Monitoring and Control of the Physiological State of Cell Cultures" Biotechnology and Bioengineering, vol. 52, pp. 271-289 (1996) (Year: 1996).

Farndale "Pulsed Electromagnetic Fields Promote Collagen Production in Bone Marrow Fibroblasts via Athermal Mechanisms" Calcif Tissue Int (1985) 37:178-182.

Aitken-Christie et al., Automation in Plant tissue culture—general introduction and overview, in Automation and Environmental Control in Plant Tissue Culture 757 (J. Aitken-Christie, T. Kozai & M. Lila Smith eds., 1995).

Apel et al., Integrated Clinical Scale Manufacturing System for Cellular Products Derived by Magnetic Cell Separation, Centrifugation and Cell Culture, Chemie Ingenieur Technik (2013).

Armstrong et al., Clinical Systems for the Production of Cells and Tissues for Human Therapy, in Novel Therapeutics From Modern Biotechnology 221 (D.L. Oxender et al. eds., 1999).

Blaeschke et al., Induction of A Central Memory and Stem Cell Memory Phenotype in Functionally Active CD4+ and CD8+ Car T Cells Produced in an Automated Good Manufacturing Practice System for the Treatment of CD19+ Acute Lymphoblastic Leukemia, Cancer Immunology, Immunotherapy vol. 67, pp. 1053-1066 (2018), published Mar. 31, 2018.

Bohnenkamp et al., Bioprocess development for the cultivation of human T-lymphocytes in a clinical scale, Cytotechnology (2002).

Bousso, T-cell activation by dendritic cells in the lymph node: lessons from the movies, 8 Nature Reviews Immunology 675 (2008) ("Bousso 2008").

Declaration from Mark Selker, Submitted in *Lonza Walkersville, Inc.* v. *Adva Biotechnology Ltd.*, United States District Court for the District of Maryland, Case No. 8:20-cv-03099-PX, Jan. 5, 2022.

Declaration from James C. Leung, Submitted in *Lonza Walkersville, Inc.* v. *Adva Biotechnology Ltd.*, United States District Court for the District of Maryland, Case No. 8:20-cv-03099-PX, Jan. 7, 2022.

Kaiser et al., Towards a Commercial Process for the Manufacture of Genetically Modified T Cells for Therapy, 22 Cancer Gene Therapy 72-78 (2015).

Kempner et al., A Review of Cell Culture Automation, 7 Journal of the Association for Laboratory Automation 56 (2002) ("Kempner 2002").

Koller et al., Clinical-scale human umbilical cord blood cell expansion in a novel automated perfusion culture system, Bone Marrow Transplantation (1998) ("Koller 1998").

Koller et al., Large-Scale Expansion of Human Stem and Progenitor Cells from Bone Marrow Mononuclear Cells in Continuous Perfusion Cultures, Blood (1993) ("Koller 1993A").

Koller et al., Tissue Engineering: Reconstitution of Human Hematopoiesis Ex Vivo, Biotechnology and Bioengineering (1993) ("Koller 1993B").

Kostov et al., Low-Cost Microbioreactor for High-Throughput Bioprocessing, 72 Biotechnology and Bioengineering, Feb. 5, 2001 ("Kostov 2001").

Krug et al., A GMP-compliant protocol to expand and transfect cancer patient T cells with mRNA encoding a tumor-specific chimeric antigen receptor, Cancer Immunol Immunotherapy (2014) ("Krug 2014").

Levine et al., Global Manufacturing of CAR T Cell Therapy, 4 Molecular Therapy: Methods & Clinical Development 92 (2017).

Lock et al., Automated Manufacturing of Potent CD20-Directed Chimeric Antigen Receptor T Cells for Clinical Use, 28 Human Gene Therapy 10 (2017), ("Lock 2017").

Lu et al., A Rapid Cell Expansion Process for Production of Engineered Autologous CART Cell Therapies, 27 Human Gene Therapy 6 (2016).

Mock et al., Automated manufacturing of chimeric antigen receptor T cells for adoptive immunotherapy using CliniMACS Prodigy, Cytotherapy (2016).

Morse, Technology evaluation: Stem-cell therapy, Aastrom Biosciences Inc., Current Opinion in Molecule Therapeutics (1999) ("Morse 1999").

Oh et al., Frequent Harvesting from Perfused Bone Marrow Cultures Results in Increased Overall Cell and Progenitor Expansion, Biotechnology and Bioengineering (1994).

(56) References Cited

OTHER PUBLICATIONS

Priesner et al., Automated Enrichment, Transduction, and Expansion of Clinical—Scale CD62L+ T Cells for Manufacturing of Gene Therapy Medicinal Products, 27 Human Gene Therapy 10, 860-869 (2016).

Rosazza et al., Gene Electrotransfer: A Mechanistic Perspective, Current Gene Therapy (2016) ("Rosazza 2016").

Shi et al., "Performance of Mammalian Cell Culture Bioreactor with a New Impeller Design" Biotechnology and Bioengineering, vol. 40, pp. 260-270 (1992).

Stiff et al., Autologous transplantation of ex vivo expanded bone marrow cells grown from small aliquots after high-dose chemotherapy for breast cancer, Blood (2000) ("Stiff 2000").

Wang et al., Clinical Manufacturing of CAR T Cells: Foundation of a Promising Therapy, 3 Molecular Therapy—Oncolytics 1 (2016).

Wang et al., Manufacture of Tumor- and Virus-specific T Lymphocytes for Adoptive Cell Therapies, 22 Cancer Gene Therapy 2 (2015).

Zhang et al., Characterization of clinical grade CD19 chimeric antigen receptor T cells produced using automated CliniMACS Prodigy system, Drug Design, Development and Therapy (2018) ("Zhang 2018").

Zhu et al., Closed-system manufacturing of CD19 and dual-targeted CD20/19 chimeric antigen receptor T cells using the CliniMACS Prodigy device at an academic medical center, Cytotherapy (2018).

\* cited by examiner

QUALITY CONTROL METHODS FOR AUTOMATED CELL PROCESSING

CROSS-REFERENCE TO RELATED APPLICATIONS

The present application claims benefit of U.S. Provisional Patent Application No. 62/933,575, filed Nov. 11, 2019, the disclosure of which is incorporated by reference herein in its entirety.

FIELD OF THE INVENTION

The present disclosure provides methods for assessing and optimizing cellular quality of a cell-based therapy that is being produced in an automated cell engineering system. The methods suitably include monitoring molecular characteristics of the cells before, during, and after the automated process to provide feedback to the process parameters. In embodiments, the cells being produced are Chimeric Antigen Receptor (CAR) T-cells.

BACKGROUND OF THE INVENTION

As anticipation builds about accelerated clinical adoption of advanced cell therapies, more attention is turning to the underlying manufacturing strategies that will allow these therapies to benefit patients worldwide. While cell therapies hold great promise clinically, high manufacturing costs relative to reimbursement present a formidable roadblock to commercialization. Thus, the need for cost effectiveness, process efficiency and product consistency is driving efforts for automation in numerous cell therapy fields, and particularly for T cell immunotherapies (see, e.g., Wang 2016).

However, significant challenges remain, preventing the widespread adoption of autologous cell therapies and causing manufacturing failures. Because a starting cell material often originates from the patient, this represents an additional level of complexity as well as a source of variability. Many patients currently treated with cell therapies have advanced disease and many times are relapsed, refractory to multiple other therapies. As a result, the therapeutic window in which patients can benefit from these cell therapies is narrow, requiring an accurate and reliable manufacturing process.

After manufacturing the cell therapy product, there are additional delays before the product can be administered to the patient, primarily a slew of regulatory requirements and release testing which are currently slow and costly. Current cell therapy release testing provides the necessary information for regulators to be comfortable with dosing patients but does little to predict clinical efficacy.

In automated processes for producing cell-based therapies, there is often a need to optimize and modify various parameters of the process based on individual patient needs, and real-time changes during the methods. The present invention fulfills these needs by providing methods of assessing and optimizing cellular quality of a cell-based therapy, suitably in automated systems.

SUMMARY OF THE INVENTION

In some embodiments provided herein is a method for assessing and optimizing cellular quality of a cell-based therapy, comprising: determining one or more molecular characteristics of a pre-modified cell culture; genetically modifying the cell culture via an automated cell engineering system; determining the one or more molecular characteristics of the modified cell culture during and after the genetically modifying; and optimizing one or more parameters of the automated cell engineering system to alter the one or more molecular characteristics of the modified cell culture.

In further embodiments, provided herein is a method for assessing and optimizing cellular quality of a cell-based therapy, comprising: determining one or more molecular characteristics of a pre-modified cell culture; optimizing one or more parameters of an automated cell engineering systems to alter one the one or more molecular characteristics of the pre-modified cell culture; activating the pre-modified cell culture with an activation reagent to produce an activated cell culture; transducing the activated immune cell culture with a vector, to produce a transduced cell culture; expanding the transduced cell culture; concentrating the expanded cell culture of (e); harvesting the concentrated cell culture of (f) to produce a genetically modified cell culture; determining the one or more molecular characteristics of the cell culture during or after any one of steps (c)-(g); and optimizing one or more parameters of any one of steps (c)-(g) to alter the one or more molecular characteristics of the cell culture.

In additional embodiments, a method for assessing and optimizing cellular quality of a chimeric antigen receptor T (CAR T) cell culture is provided, comprising: determining one or more molecular characteristics of a pre-modified T-cell culture; optimizing one or more parameters of an automated cell engineering system to alter one the one or more molecular characteristics of the pre-modified T-cell culture; activating the pre-modified T-cell culture with an activation reagent to produce an activated T-cell culture; transducing the activated T-cell culture with a vector encoding a chimeric antigen receptor, to produce a CAR T-cell culture; expanding the CAR T-cell culture; concentrating the expanded CAR T-cell culture of (e); harvesting the concentrated CAR-T cell culture of (f); determining the one or more molecular characteristics of the CAR T-cell culture during or after any one of steps (c)-(g); and optimizing one or more parameters of any one of steps (c)-(g) to alter the one or more molecular characteristics of the CAR T-cell culture.

Also provided herein is a method for assessing and optimizing cellular quality of a cell culture, comprising: determining one or more molecular characteristics of a pre-modified cell culture; genetically modifying the cell culture via an automated cell engineering system; determining the one or more molecular characteristics of the modified cell culture during and after the genetically modifying; and optimizing one or more parameters of the automated cell engineering system to alter the one or more molecular characteristics of the modified cell culture.

DETAILED DESCRIPTION OF THE INVENTION

The present disclosure provides methods for the monitoring, assessing, and optimizing of the automated production of various cell-based therapies.

Automated Cell Processing

For autologous cell-based therapies and treatments, such as T cell therapy, the need for cost effectiveness, process efficiency, and product consistency is particularly acute, as manufacturing micro-lot (one patient per lot) batches lacks the economies of scale that allogeneic (multiple patients per lot) processes can exploit (see, e.g., Jones 2012; Trainor 2014). The larger and more localized workforce and facilities required for micro-lots places considerable demands on logistics, GMP compliance for manual production, especially with respect to availability and training of staff. In addition, the potential for variability in technique between operators can pose an undesirable risk to consistently meeting release criteria and ensuring a safe and dependable product.

As described herein, installation and comprehensive validation of automated manufacturing provides a solution to these logistical and operational challenges. An important approach to introducing automation to a production process is identifying the key modular steps where the operator applies a physical or chemical change to the production material, termed "unit operations." In the case of cell manufacturing, this includes steps such as cell separation, genetic manipulation, proliferation, washing, concentration, and cell harvesting. Manufacturers often identify focal process bottlenecks as the immediate opportunities for introducing automation. This is reflected in the technical operation spectrum of the majority of commercially available bioreactors, which tend to focus on discrete process steps. Process challenges in cell manufacturing (from sterility maintenance to sample tracking) are addressed herein by end-to-end automation that generates consistent cellular outputs while ameliorating inevitable process variability. The methods described herein also provide simplification, and the associated electronic records aid in complying with GMP standards (see, e.g., Trainor 2014).

Automation of Unit Operations and Key Process Sensitivities

The recent rapid progress of the clinical development of various cell-based therapies, including modified autologous T cells for cancer immunotherapy, has led to planning for the associated translation and scale up/out implications.

Figure 1:
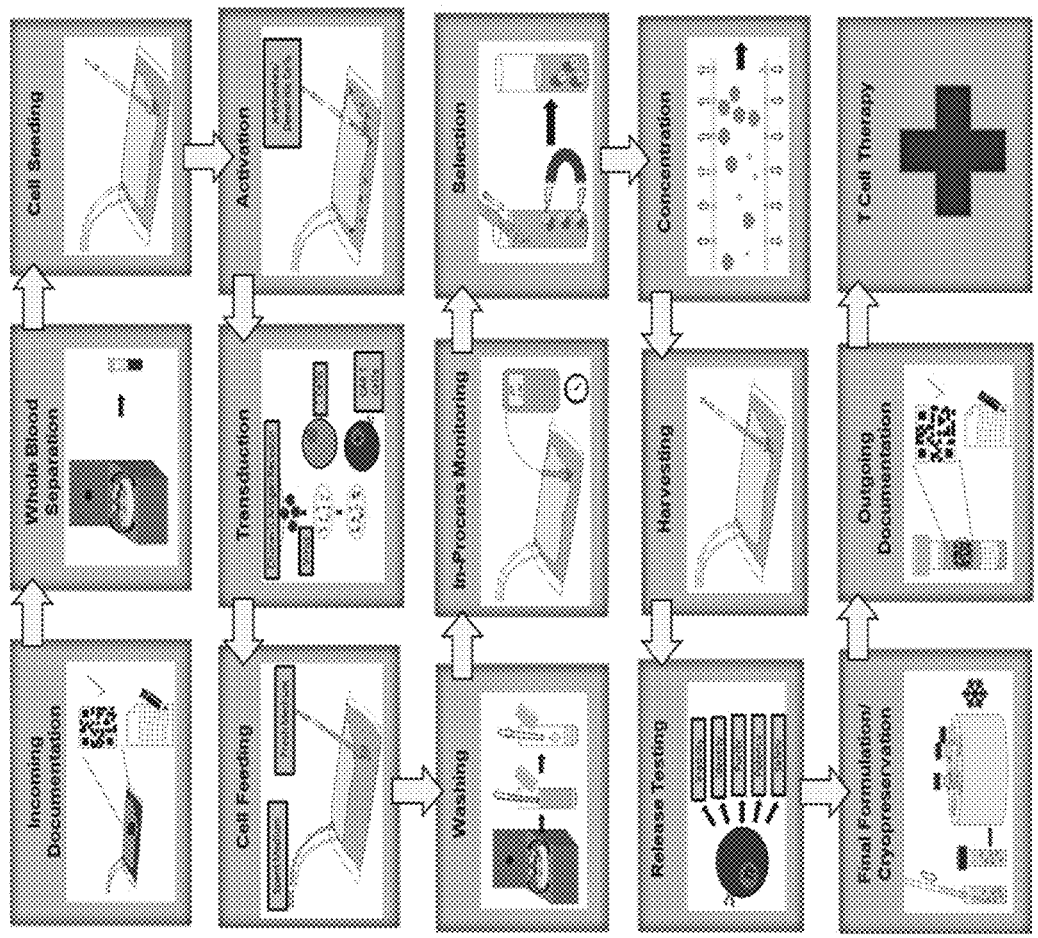
FIG. 1 shows a generalized manufacturing process for producing a cell-based therapy as described herein.

While specific protocols will vary for different cell-based therapies, a generalized process is illustrated in FIG. 1. FIG. 1 describes unit operations of cell-based therapy manufacturing, from initial processing of a patient blood sample to formulating output cells, including for example for autologous T cell therapy.

As described herein, to achieve cell manufacturing automation, the methods described herein provide for understanding the status of the cells at each transition point and how they are impacted by the specific unit operation. The micro-lot production for patient-specific therapies should be respectful of key process sensitivities that impact the feasibility of automation. Automation described herein successfully embraces various process steps.

Table 1 below highlights the challenges of some process steps identified for cell-based therapy automation, including T cell automation, and notes the impact of the sensitivity on the automation strategy. Note that for all unit operations, open transfer of cells between respective equipment is a key sensitivity due to the risk of contamination.

TABLE 1

Automation Challenges and Benefits

| Unit Operation | Challenges of Key Process Steps | Benefit of Automating |
|---|---|---|
| Fractionation | Highly variable based on donor cells and operator technique (see e.g., Nilsson 2008) Residual impurities can impact performance | High purity of target starting population More consistent and improved product |
| Cell Seeding | Inhomogeneous cell distribution leads to variability in growth rates | Homogenous automated seeding strategy can improve consistency and potency |
| Activation | Stable contact between cells and activation reagent Uniform activation - homogeneous distribution | Automated loading can ensure reproducibly homogeneous distribution and activation which can be difficult to consistently achieve with manual methods |
| Transduction | Efficiency can be affected by the degree of cell-virus mixing, which may vary based on operator handling Increased exposure time may have negative impact on cells | Volume reduction prior to virus addition enables high degree of cell-virus contact Time-based operation enables cell transfer regardless of time of day Closed system decreases risk to operator |
| Electroporation | Efficiency can vary based on operator mixing, washing and concentration technique | Standardized protocols ensure consistent results when upstream and downstream steps are integrated |
| Feeding | Timing of media exchange needs to consider nutritional requirements based on cell growth (see, e.g., Bohenkamp 2002), and the component stability at 37° C. | Biofeedback can optimize feeding schedule (see, e.g., Lu 2013) and minimize media use Components can be stored at refrigerated temperatures to prolong stability and automatically pre-warmed before use |
| Selection | Extensive handling steps can result in cell loss Operator variability | Full automation improves consistency |
| Harvest | Acellular materials (such as cell separation beads) to be removed prior to final formulation (see e.g., Hollyman 2009) Manual pipetting variability can impact final yield | Cells automatically transferred from culture vessel regardless of time of day Improved final yield consistency over manual pipetting |
| Washing | Aggressive washing may induce shear stress or cause cell loss during supernatant removal | Gentle washing, filtration, or sedimentation without moving the culture vessels, can be utilized to reduce cell loss and remove residuals |
| Concentration | Cell recovery may vary by operator during aspiration | Automated volume reduction reduces operator variability Filtration methods also minimize cell loss |
| Formulation | Product must be well mixed Small working volumes magnify impact of volume inaccuracies Viability decreases with longer exposure times to cryopreservative | Automated mixing ensures homogenous distribution of cells in final formulation Automated volume addition removes risk of manual pipetting error or variability Increased automation reduces variability in temperature sensitive steps |

Tailoring the automation of a manual process around the sensitivities listed in Table 1 can support successful translation, maintenance or improvement on the performance of the cell therapy.

Discrete Versus Fully Integrated Automation

While there is compelling evidence for the value of automation (see, e.g., Trainor 2014; Levine 2017), there needs to be a subsequent analysis on the value and practicality of integrating these automation steps in an end-to end sequence with automated transfers. There are different perspectives on the advantages of discrete process automation versus the advantages of end-to-end integration.

The key benefit to discrete automation is flexibility. This relates to the areas of:
1) Maintenance of unique process operations
2) Acceleration of translational activities based on individual unit operation validation
3) Ability to modify processing steps to accommodate donor-to-donor variability The first point related to increased flexibility provides the operator with more control of the process. This is important in circumstances where the process has highly sensitive steps that can impact the final product. Switching to an all-in-one system may impose constraints that influence the product outcome. A discrete approach provides the flexibility to choose how to perform each step, which may be particularly important with highly sensitive unit operations. The discrete approach also allows gradual translation into automation from manual processing, which helps to demonstrate equivalency if each unit operation can be tested independently. Additionally, automating specific unit operations provides the flexibility for decisions to be made based on the cell performance. For example, if cells are growing rapidly, there may be the need to expand from one cell culture bag to two. Lastly, the approach to automation using discrete systems also enables groups to pick-and-choose which equipment to use for each unit operation.

Equipment utilization is another argument for discrete automation. There may be some unit operations that require significantly more time than others. An end-to-end processing system requires all multiple unit operations to run on a single system, thus occupying the equipment for the duration of the culture process.

While there are benefits to discrete automation, an end-to-end approach offers different, though no less compelling benefits. Firstly, a fully integrated system greatly reduces the risk of contamination. As there is increased handling required with a discrete approach, there is a greater chance of product variability due to operator interventions. Secondly, and as previously mentioned, this inevitably leads to higher labor costs.

The flexibility provided by the discrete approach is important. In situations where the process is important in defining the product, an end-to-end system should have the flexibility to integrate unique sensitivities. This may include certain feeding strategies, oxygen levels, surface treatments, and so forth. Such an approach requires flexibility in both the software and the disposable component. The system should provide the option to pull cell and media samples at various points in the process to confirm that specific unit operations meet product specification checkpoints. If modifications need to be made, the software should be able to implement these changes to provide ideal conditions. While easy-to-use and flexible software is highly beneficial for translational purposes, it is important that the software can be easily locked down to comply with clinical standards (FDA 21 CFR Part 11). Once locked down, there should be limited if any ability for the operator to change the protocol. However, to address issues with inherent donor-variability, there should be the option to select from a range of validated protocols based on cell growth rates. For example, if the cells are growing rapidly, the system should be able to respond to this and adjust the feed or harvest time points, accordingly.

Figure 2:
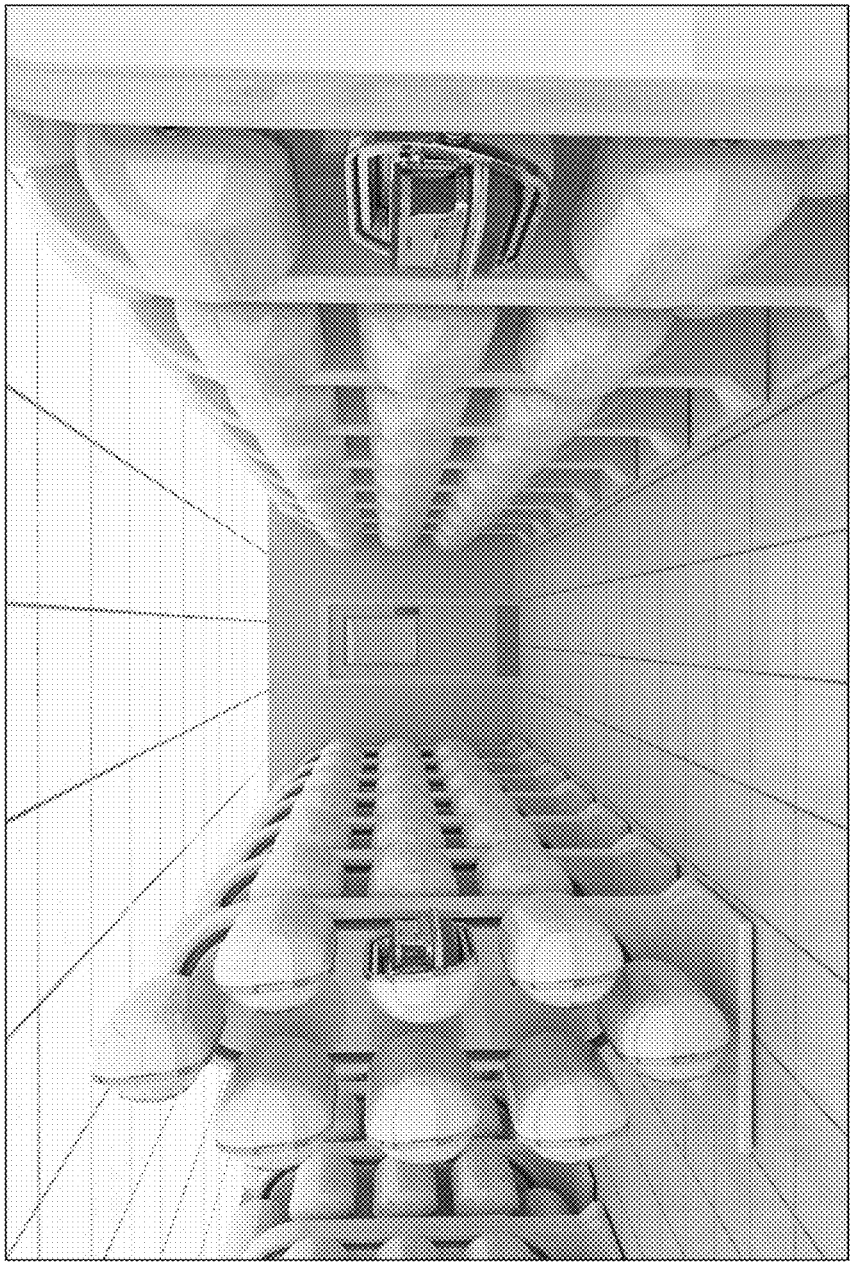
FIG. 2 shows a lab space containing exemplary cell engineering systems as described in embodiments herein.

The selection of end-to-end integration versus discrete automation is also dependent upon the long-range vision for the clinical process. A single all-in-one system can offer significantly greater space efficiency to minimize the required footprint in expensive GMP clean rooms. For example, as shown in FIG. 2, fully integrated automated systems are designed to maximize required footprint to reduce expensive GMP clean room space. FIG. 2 shows 96 patient-specific end-to-end units running in a standard lab space.

A single system also provides greater ease of data tracking, whereas discrete systems may not offer compliant software that links together all electronic data files. Software platforms such as VINETI (Vineti Ltd) and TRAKCEL (TrakCel Ltd) allow electronic monitoring and organization of supply chain logistics. However, single all-in-one culture systems can go further still by incorporating a history of both processing events and biomonitoring culture conditions associated with each unit operation into a batch record. Accordingly, the benefits of end-to-end integration offer a significant competitive advantage.

Commercial Platforms for Integration of Unit Operations

Clinical trial success in a number of autologous cell therapies, especially immunotherapy for blood-based cancers, has highlighted the importance of enabling translation of new clinical protocols to robust production platforms to meet projected clinical demand (see, e.g., Levine 2017; Locke 2017). For autologous therapies, processing each patient-specific cell treatment suitably utilizes comprehensive manufacturing activities and operations management. The methods herein link unit operations in a turnkey automated system to achieve process optimization, security and economy.

The challenge in designing an autologous process is two-fold. Firstly, unlike allogeneic manufacturing in which separate processing steps can occur in physically separate and optimized pieces of equipment, scaled-out autologous platforms suitably perform all of the necessary steps in a single closed, self-contained automated environment. Secondly, unlike an allogeneic process in which every run theoretically starts with a high-quality vial from a cell bank, with known quality and predictable process behavior, the starting material in an autologous process is highly variable, and generally comes from individuals with compromised health.

Thus, provided herein are methods that are able to sense culture conditions and respond accordingly as a sophisticated bioreactor, by controlling factors such as physical agitation, pH, feeding, and gas handling. Furthermore, there are significantly different challenges with technology transfer related to autologous treatments compared to allogeneic treatments. Autologous products may have greater restrictions on stability between the manufacturing process and the patient treatment. Sites can be located globally rather than at a single center. Having a locked down (e.g., fully enclosed) all-in-one system significantly improves the technology transfer process between sites.

While source variability cannot be eliminated, automation helps to remove variability of the final autologous product through standardization and reproducibility. This practice is adopted by leading cell system providers to obtain a cell performance reference point via biosensors that monitor the status of the active cell cultures. In end-to-end integration, output from any specific stage in the process should be within acceptable parameters for the onward progression of the process.

As described herein, in embodiments, the methods provided utilize the COCOON platform (Octane Biotech (Kingston, ON)), which integrates multiple unit operations in a single turnkey platform. Multiple cell protocols are provided with very specific cell processing objectives. To provide efficient and effective automation translation, the methods described utilize the concept of application-specific/sponsor-specific disposable cassettes that combine multiple unit operations—all focused on the core requirements of the final cell therapy product.

Figure 3:
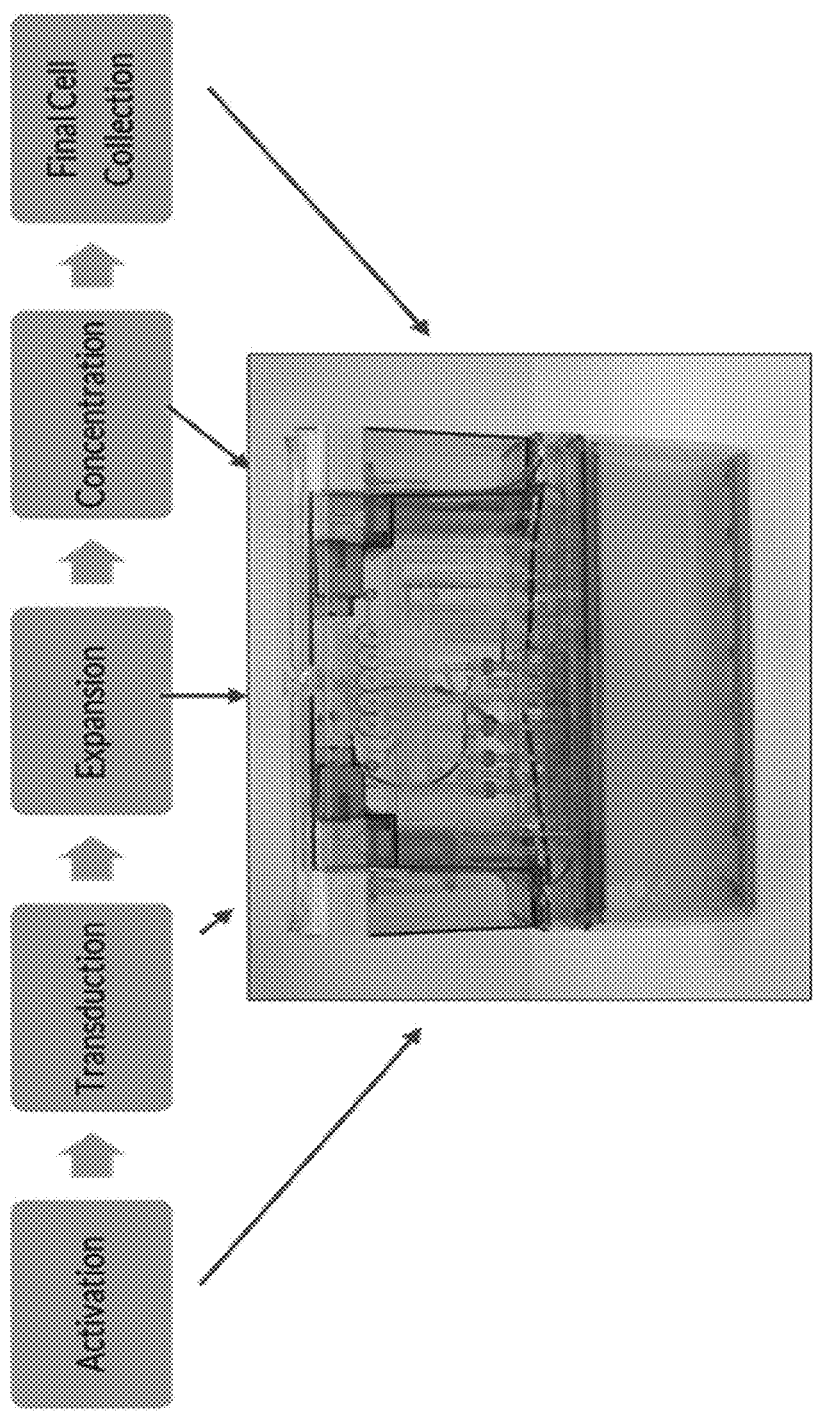
FIG. 3 shows a cell-based therapy production process that can be performed in a cell engineering system as described in embodiments herein.

The methods described herein have been used to expand various cell-based therapies, including CAR T cells (including activation, viral transduction and expansion, concentration and washing), in a fully-integrated closed automation system (FIG. 3).

Advantages of Automation

Automation of unit operations in cell therapy production provides the opportunity for universal benefits across allogeneic and autologous cell therapy applications. In the unique scenario of patient-specific, autologous cell products, and ever more emphasized by the recent clinical success of these therapies, the advantages of automation are particularly compelling due to the significant micro-lot complexities of small batch GMP compliance, economics, patient traceability and early identification of process deviations. The associated emergence of complex manufacturing protocols draws attention to the fact that the value of end-to-end integration of automated unit operations in micro-lot cell production has not been a point of significant study. However, the expected demand for these therapies following their impending approval indicates that implementation of a fully closed end-to-end system can provide a much needed solution to manufacturing bottlenecks, such as hands-on-time and footprint.

Developers of Advanced Therapies are encouraged to consider automation early in the rollout of clinical translation and scale up of clinical trial protocols. Early automation can influence protocol development, avoid the need for comparability studies if switching from a manual process to an automated process at a later stage, and provide a greater understanding of the longer-term commercialization route.

Quality Control of Automated Systems for Producing Cell-Based Therapies, Including CAR T Cells As described herein, methods are provided that allow for the monitoring, assessing, and optimizing of the automated production of various cell-based therapies. The methods described herein include monitoring various molecular characteristics at different times before, during, and after the automated processes, and making changes and adjustments to various parameters of the automated systems to optimize output. Such optimizations can be based on a desired cell number, concentration, or characteristic for a particular therapy or even an individual patient.

Thus, in embodiments, provided herein is a method for assessing and optimizing cellular quality of a cell-based therapy. As used herein "assessing" refers to the act of measuring or determining one or more characteristics of a cell, including a molecular characteristic of a cell, to help guide any changes to the methods. As used herein "optimizing" refers to modifying one or more parameters of the automated cell engineering systems described herein. As used herein "cellular quality" refers to the characteristics necessary for a cell to operate as desired in the cell-based therapy. This quality includes membrane integrity, nucleus integrity, desired gene profile, desired protein profile, desired cellular life, desired cellular number or density, etc.

As used herein a "cell-based therapy" refers to a therapy in which cellular material is injected, grafted or implanted into a patient. Cell-based therapies suitably include intact, living cells. Cell-based therapies include various types of cells, such as immune cells, natural killer cells, cells for a neurodegenerative therapy, and stem cells. The methods described herein may be used suitably for any cell type used for cell-based therapies or cell culture generally, which may include tissue engineering applications and cell cultivation for biologic production such as viral vector or protein expression.

The methods for assessing and optimizing cellular quality of a cell-based therapy suitably include determining one or more molecular characteristics of a pre-modified cell culture. As used herein "molecular characteristics" include one or more of a genetic profile (e.g., a gene expression profile), an amino acid or protein profile (e.g., proteins expressed within or on the surface of a cell), a lipid profile, etc., of a cell. As used herein a "cell culture" refers to single cells as well as collections of cells for use in the automated methods described herein.

The methods suitably begin with determining one or more molecular characteristics of a pre-modified cell culture. That is a cell culture that has not yet been placed into the automated cell engineering systems described herein. A pre-modified cell culture can include cells taken directly from a patient (e.g., a blood draw, or plasma sample), as well as cells that have been removed from a patient and undergone some filtering, selection or other modifications to arrive at a desired cell culture population that is to be modified in the automated cell engineering systems described herein.

The methods suitably include genetically modifying the cell culture via an automated cell engineering system. As used herein "genetically modifying" includes introducing one or more genes into a cell (e.g., via transduction) to suitably modify the genome of the cell. Genetic modifying can also include transient modifications, which do not integrate into the genome. Methods for genetically modifying a cell culture are described herein and suitably include activating a cell culture with an activation reagent to produce an activated immune cell culture, transducing the activated cell culture (e.g., with a vector), to produce a transduced cell culture and expanding the transduced immune cell culture (see, e.g., FIGS. 1 and 3). Methods for preparing, activating, transducing, and expanding a cell culture are described herein.

In exemplary embodiments, the methods for assessing and optimizing cellular quality suitably further include determining the one or more molecular characteristics of the modified cell culture during and after the genetic modifying. That is, at any point during any one of the activating, transducing and/or expanding, the cell culture can be assessed, and suitably one or more molecular characteristics of the cell culture are determined. This sampling and assessment provides data on the characteristics of the cell culture at various points during the automated processing, as well as after the automated processing, allowing for tracking one or more molecular characteristics at each stage of the automation.

The methods for assessing and optimizing cellular quality suitably further include optimizing one or more parameters of the automated cell engineering system to alter the one or more molecular characteristics of the modified cell culture. As described herein, the parameters of the automated cell engineering system that can be optimized include processing parameters (e.g., pH, temperature, heat), as well as quality and duration of activation, transduction, and expansion, cell selection, etc.

In exemplary embodiments, the one or more molecular characteristics include one or more of a gene expression, a protein expression, an mRNA expression, and a copy number variation.

Suitably, the molecular characteristics are determined by one or more methods for multiplex analysis of RNA, DNA and/or protein targets of the cell-based therapy and/or the cell culture. Exemplary multiplex analysis tools include various arrays, barcode technologies, next generation sequencing approaches, quantitative PCR, etc.

In exemplary embodiments, the molecular characteristics can be determined using an approach such as the molecular barcode approach NCOUNTER®, developed by NANOSTRING® (Seattle, WA). The molecular barcode approach utilizes a unique capture probe designed to bind to the desired target (e.g., nucleic acid (RNA, DNA), protein, or peptide). A reporter probe that includes a barcode (e.g., a fluorescent-based, color-based, or radioactive-based tag) binds to the capture probe. The sample is purified and immobilized, and the barcoded target molecules are then counted and analyzed. See, e.g., Geiss, et al, "Direct multiplexed measurement of gene expression with color-coded probe pairs," *Nat. Biotechnol.* 26:317-325 (2008), the disclosure of which is incorporated by reference herein in its entirety.

As described herein, the cell cultures that can be utilized in the automated cell engineering systems described herein include immune cell cultures, natural killer cell cultures, and cell cultures for a neurodegenerative therapy.

In exemplary embodiments, the immune cell culture is a T-cell culture, and in embodiments is a chimeric antigen receptor T (CAR T) cell culture. A chimeric antigen receptor T cell, or "CAR T cell," is a T cell that is modified with a chimeric antigen receptor (CAR) to more specifically target cancer cells. In general, a CAR includes three parts: the ectodomain, the transmembrane domain, and the endodomain. The ectodomain is the region of the receptor that is exposed to extracellular fluid and includes three parts: a signaling peptide, an antigen recognition region, and a spacer. The signaling peptide directs the nascent protein into the endoplasmic reticulum. In CAR, the signaling peptide is a single-chain variable fragment (scFv). The scFv includes a light chain ($V_L$) and a heavy chain ($V_H$) of immunoglobins connected with a short linker peptide. In some embodiments, the linker includes glycine and serine. In some embodiments, the linker includes glutamate and lysine.

The transmembrane domain of the CAR is a hydrophobic α-helix that spans the membrane. In some embodiments, the transmembrane domain of a CAR is a CD28 transmembrane domain. In some embodiments, the CD28 transmembrane domain results in a highly expressed CAR. In some embodiments, the transmembrane domain of a CAR is a CD3-ζ transmembrane domain. In some embodiments, the CD3-ζ transmembrane domain results in a CAR that is incorporated into a native T cell receptor.

The endodomain of the CAR is generally considered the "functional" end of the receptor. After antigen recognition by the antigen recognition region of the ectodomain, the CARs cluster, and a signal is transmitted to the cell. In some embodiments, the endodomain is a CD3-ζ endodomain, which includes 3 immunoreceptor tyrosine-based activation motifs (ITAMs). In this case, the ITAMs transmit an activation signal to the T cell after antigen binding, triggering a T cell immune response.

During production of CAR T cells, T cells are removed from a human subject, genetically altered, and re-introduced into a patient to attack the cancer cells. CAR T cells can be derived from either the patient's own blood (autologous), or derived from another healthy donor (allogenic). In general, CAR T cells are developed to be specific to the antigen expressed on a tumor that is not expressed in healthy cells.

In exemplary embodiments, the one or more molecular characteristics include one or more of a gene expression, a protein expression, an mRNA expression, and a copy number variation of a CAR T cell. In additional embodiments, the one or more molecular characteristics relate to T-cell activation, metabolism, exhaustion, and T-cell receptor diversity.

Suitably, the molecular characteristics are determined using the molecular barcode approach NCOUNTER®, developed by NANOSTRING® (Seattle, WA), with a CAR T Characterization panel. Exemplary characteristics of the CAR T Characterization panel include the ability to review the expression of about 500-1000 genes, suitably about 700-800 genes, including about 700, about 750, about 760, about 770, about 780, about 790, about 800 or about 850 human genes. The genes include eight of the components of CAR T cell biology including T cell activation, metabolism, exhaustion, TCR receptor diversity and transgene expression.

The molecular characteristics are suitably determined using a non-enzymatic, non-amplified barcoded technology (e.g., NCOUNTER®) that allows for direct digital detection of molecules with up to 6-logs of dynamic range. With just 15 minutes total hands on time and data in less than 24 hours, the workflow provides a boost in productivity when compared to either next generation sequencing (NGS) or quantitative PCR (qPCR) approaches. Both of these can take days to weeks longer and can include library preparation, DNA synthesis and amplification all of which require additional hands-on time, potential user error and reproducibility challenges introduced through the use of enzymes. Data produced from the barcoded technology results in direct counts of molecules, does not require a specialized bioinformatician, and is amendable to simple analysis visualizations and reports, through various analysis software or through other customized reports.

The nCounter CAR-T Characterization panel which measures gene expression on the nCounter platform was created for use specifically within the field of cell therapy to further enable characterization, optimization and signature development to profile various stages in manufacturing and allow for better control of the process which can in turn address the challenges around consistent and reproducible manufacturing of cell therapies. The nCounter CAR T Characterization Panel was created in collaboration with 8 leading centers in the field of CAR T therapy and is designed for use across the entirety of the CAR T work flow, enabling uniform and robust profiling of leukapheresis, manufactured product and post infusion CAR T cells The customizable, 780 gene expression panel incorporates content to measure 8 essential components of CAR T cell biology including T cell activation, metabolism, exhaustion, and TCR receptor diversity with optional customization for measuring transgene expression.

The following table provides exemplary information obtainable from the CAR T characterization panel (see nanostring.com; car-t-characterization panel):

| CAR-T Biology | Description | Pathway or Process |
|---|---|---|
| Phenotype | Cytokines and pathways that maintain, promote, and modulate their activity. | Notch, Wnt signaling, Tfh, TGF-beta, Th1, Th17, Th2, Th9, Treg, Innate-like T-cells, Vitamin A (RA) Signaling |
| Cell Types | Identification of contaminating cell types. | Immune cell profiling |
| TCR Diversity | Number of clones present after leukapheresis, manufacturing, and infusion. | TCR Content |
| Activation | By antigens presented to the TCR complex and modulated by costimulatory molecules. | Chemokine Signaling, Costimulatory Molecules, Interleukin Signaling, TCR signaling, JAK-STAT, MAPK and PI3K Signaling, Myc targets, NFAT, Antigen processing & presentation, T-cell activation markers |
| Metabolism | Metabolic pathways, including carbohydrate and fatty acid metabolism. | Glycolysis, Mitochondrial biogenesis, Fatty Acid Metabolism Glutamine metabolism, Circadian Clock, One-carbon metabolism, Oxidative phosphorylation, mTOR, Cell Cycle, Autophagy |
| Persistence | Molecules involved in T cell migration | T-cell migration, T-cell cell type profiling |
| Exhaustion | T-cell exhaustion can be induced by costimulatory molecules, other cell-cell interactions, and cell death via apoptosis. | T-cell exhaustion markers, Apoptosis, Interactions with Non-Lymphoid Cells, Costimulatory Molecules |
| Toxicity | Potential for off-target toxicities of CAR-T treatment. | NK cell cytotoxicity, NKT Receptors, NF-kB, Type 1 interferon signaling Type II interferon signaling, Interleukin signaling, Chemokine signaling |

The genes included in a CAR T characterization panel can include the following (see nanostring.com; car-t-characterization panel):

| Cell Type | Panel Genes |
|---|---|
| B Cells | BLK, CD19, CD20, TNFRSF17 |
| T Cells | CD3D, CD3E, CD3G, CD6, SH2D1A |
| TH1 | TBX21 |
| Regulatory T Cells (Tregs) | FOXP3 |
| CD8+ T Cells | CD8A, CD8B |
| Exhausted CD8+ T Cells | CD244, EOMES, CD223 |
| Cytotoxic Cells | CTSW, GNLY, GZMA, GZMB, GZMH, CD161, CD94, KLRK1, PRF1 |
| Dendritic Cells | CCL13, CD209, HSD11B1 |
| Macrophages | CD163, CD68, CD84 |
| Mast Cells | MS4A2, TPSAB1 |
| Neutrophils | CSF3R, CD16, S100A12 |
| Natural Killer (NK) Cells | NKP46, XCL2 |
| NK CD56dim cells | IL21R, KIR2DL3, KIR3DL1, KIR3DL2 |

For the CAR T characterization panel, sample input can include sorted T-Cells (e.g., before the genetic modification steps), CAR-T cells (e.g., after the final steps of the automated processes), a CAR-T manufacturing product (e.g., cells during different stages of the automated process), whole blood, or nucleic acids.

Based upon the information obtained from the molecular characteristics, one or more optimizations can occur in the automated processes. These optimizations can occur before, during, and/or after the genetically modifying steps of the automated process.

The optimizations can include one or more of increasing or decreasing a flow rate of cell media, increasing or decreasing oxygen concentration, increasing or decreasing carbon dioxide concentration, increasing or decreasing a glucose level, increasing or decreasing the temperature of a cell expansion, increasing or decreasing the pH of a cell media, modifying a cell transduction procedure, modifying a vector for use in a transduction procedure, and modifying a cell isolation procedure.

Methods for optimizing the automated processes include optimization of cell culture conditions before beginning an automated method, as well as the use of feedback from various sensors, etc., to assist with real-time modifications to growth conditions (e.g., gas concentration, media conditions, temperature, pH, waste and nutrient concentrations, etc.), in combination with the information gathered regarding the molecular characteristics.

As described herein, the optimizing the one or more parameters of the automated cell engineering system suitably alters the one or more molecular characteristics of the modified cell culture. That is, the changes that are made to the automated cell engineering system (e.g., changing gas concentration, media conditions, temperature, pH, waste and nutrient concentrations, etc.), changes the molecular characteristics of the cell culture such that the optimized cell culture has improved properties. These improved properties can include, for example, a higher antigen concentration, a more efficient or complete transduction, or a higher cell density or higher cell count. Additional improved properties can manifest at the genetic level, including for example, cells with enhanced longevity, or improved characteristics for a particular patient, etc.

In embodiments, the optimizing process is a self-adjusting process, that is one that does not require input from an external (human) user, and is able via various computer programs and conditions to determine the required modifications to a cell culture or other characteristics to optimize the automated process. In embodiments, the self-adjusting process includes monitoring with one or more of a temperature sensor, a pH sensor, a glucose sensor, an oxygen sensor, a carbon dioxide sensor, and an optical density sensor. These self-adjusting processes can also monitor one or more molecular characteristics as described herein, providing a real-time feedback to the automated system either before the automated process begins, during the automated process, or after the process has ended.

As described herein, the use of these various sensors in the fully enclosed cell engineering system occurs at various times and locations within the system, and work together in concert to provide the optimization. For example, the self-adjusting process can adjust (e.g., raise or lower) one or more of a temperature, a pH level, a glucose level, an oxygen level, a carbon dioxide level, and an optical density of the transduced T cell culture, based on the monitoring.

Figure 4:
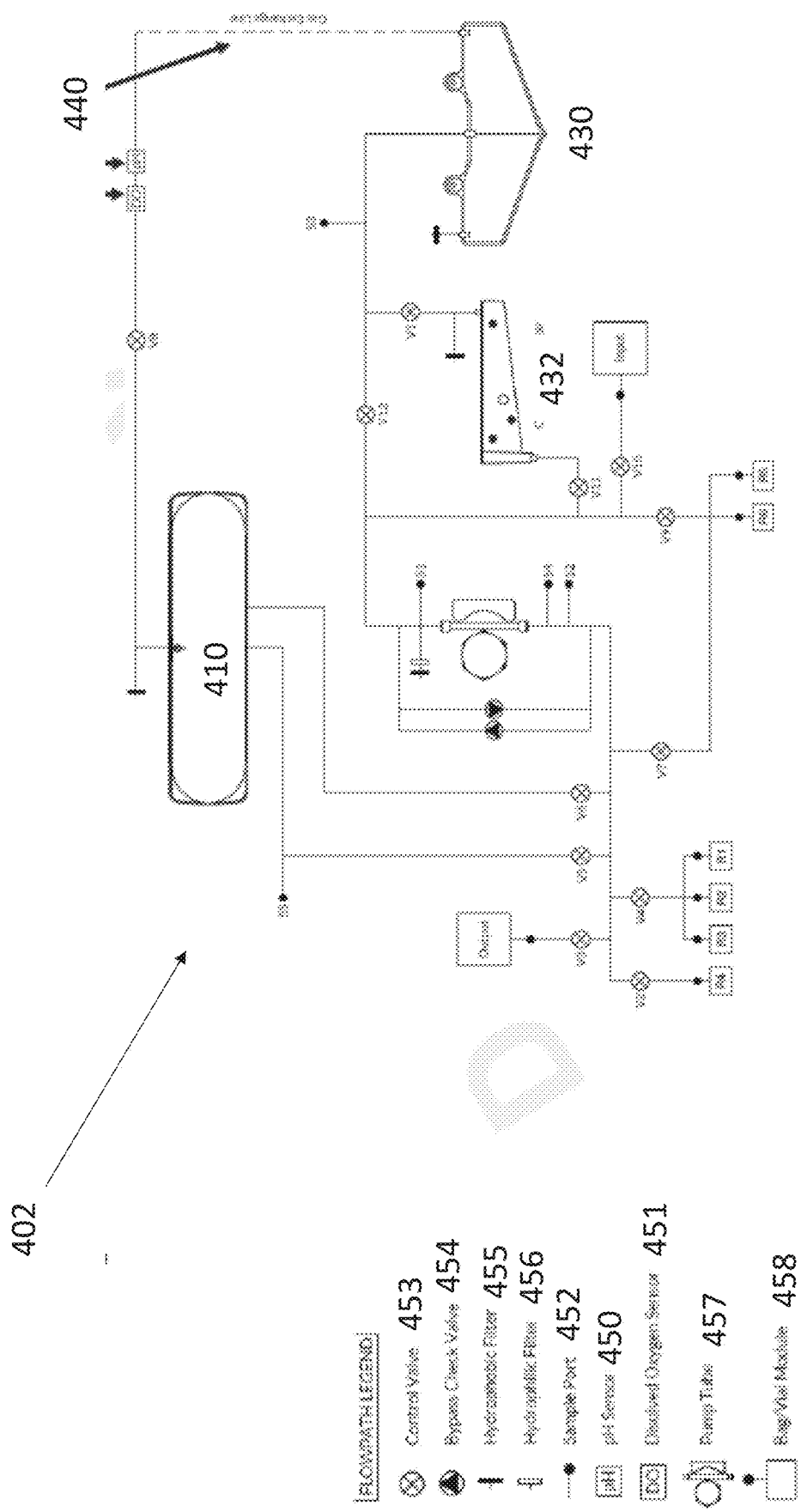
FIG. 4 shows process flow legend for an automated cell engineering system.

FIG. 4 shows a process flow legend for an automated cell engineering system as described herein, including the positioning of various sensors (e.g., pH sensor 450, dissolved oxygen sensor 451), as well as sampling/sample ports 452 and various valves (control valves 453, bypass check valves 454), as well as one or more fluidic pathways 440, suitably comprising a silicone-based tubing component, connecting the components. Also shown in FIG. 4 is the use of one or more hydrophobic filters 455 or hydrophilic filters 456, in the flow path of the cassette 402, along with pump tube 457, bag/valve module 458, control valves 432 and satellite bag 430. Also shown is the positioning of a cell culture chamber 410 within the flow path.

The optimization processes can also be based on the unique characteristics of the starting cell population, including for example, the total cell number, the source of the cells, the density of the cells, the age of the cells, as well as the molecular characteristics of the cells (including CAR T cells) determined as described herein. These starting cell population characteristics can be input into a computer control system prior to beginning the automated methods, upon which the system will make various initial modifications to optimize the methods, e.g., oxygen and carbon dioxide concentration, flow rates, incubation times, pH, etc. Alternately, the monitoring of cell processes enables the automated characterization of the progress of the cell culture sequence from the starting population to enable case-by-case adjustment of conditions for optimized final cell culture properties.

While the optimization parameters and modifications described herein are generally applicable to the COCOON® automated cell engineering system, it should be understood that such optimizations can be applied to other automated cell engineering systems. In general, control of media flow rate, gas concentration and pH, etc., are all parameters that can be controlled and optimized, regardless of the type of automated cell engineering system utilized.

In exemplary embodiments, the methods described herein produce at least about 50 million viable genetically modified immune cells. In suitable embodiments, the methods described produce at least about 100 million viable genetically modified immune cells, or at least about 200 million cells, at least about 300 million cells, at least about 400 million cells, at least about 500 million cells, at least about 600 million cells, at least about 700 million cells, at least about 800 million cells, at least about 1 billion cells, at least about 1.1 billion cells, at least about 1.2 billion cells, at least about 1.3 billion cells, at least about 1.4 billion cells, at least about 1.5 billion cells, at least about 1.6 billion cells, at least about 1.7 billion cells, at least about 1.8 billion cells, at least about 1.9 billion cells, at least about 2 billion cells, least about 2.1 billion, at least about 2.2 billion, at least about 2.3 billion, at least about 2.4 billion, at least about 2.5 billion, at least about 2.6 billion, at least about 2.7 billion, at least about 2.8 billion, at least about 2.9 billion, or at least about 3.0 billion genetically modified immune cells. In some aspects, the methods can be used to produce greater than about 3 billion genetically modified immune cells, such as for example 10 billion cells, 12 billion cells, or 15 billion cells. Suitably, but without limitation, these genetically modified immune cells are CAR T cells.

As described herein, the genetically modified immune cell culture produced by the methods is suitably a T cell culture, including a chimeric antigen receptor T (CAR T) cell culture. In such embodiments, the vector utilized to produce such CAR T cells is a vector encoding a chimeric antigen receptor. Suitably the immune cell culture comprises peripheral blood mononuclear cells and/or purified T cells. In embodiments, the immune cell culture comprises at least one accessory cell, suitably a monocyte or a monocyte-derived cell. As described herein, in embodiments, the accessory cell comprises antigens for a T cell receptor, including CD28, CD40, CD2, CD40L and/or ICOS.

The methods described herein can also provide information regarding molecular characteristics of a cell-based therapy before, during, or after a genetic modification, that is found to correlate with either low or high efficacy, or either low or high toxicity or side effects. Thus, the methods will provide quality control information before, during, or after the automated process that can be used to determine if a cell-based therapy should be administered to a patient, or if instead, there is a higher probability of problems if such a cell population is utilized.

In additional embodiments, information regarding molecular characteristics of a cell-based therapy can also be determined after the prepared cell-based therapy has been administered to a patient. For example, a patient's blood can be drawn and molecular characteristics of the desired cell type(s) can be determined, enabling improved monitoring of efficacy and increased insight into how to link a clinical outcome to cellular characteristics and an automated cell engineering process.

In further embodiments, provided herein is a method for assessing and optimizing cellular quality of a cell-based therapy, comprising: determining one or more molecular characteristics of a pre-modified cell culture; optimizing one or more parameters of an automated cell engineering system to alter one the one or more molecular characteristics of the pre-modified cell culture; activating the pre-modified cell culture with an activation reagent to produce an activated cell culture; transducing the activated immune cell culture with a vector, to produce a transduced cell culture; expanding the transduced cell culture; concentrating the expanded cell culture; and harvesting the concentrated cell culture to produce a genetically modified cell culture.

As described herein, the methods suitably include determining the one or more molecular characteristics of the cell culture during or after any one of steps of activating, transducing, expanding, concentrating or harvesting; and optimizing one or more parameters of any one of these steps to alter the one or more molecular characteristics of the cell culture.

As described herein, the one or more molecular characteristics suitably include a gene expression, a protein expression, an mRNA expression, and a copy number variation.

Exemplary cell cultures include immune cell cultures, such as a natural killer cell culture, and a cell culture for a neurodegenerative therapy. In suitable embodiments, the immune cell culture is a T-cell culture, including a chimeric antigen receptor T (CAR T) cell culture. In such embodiments, the one or more molecular characteristics include T-cell activation, metabolism, exhaustion, and T-cell receptor diversity.

Figure 5:
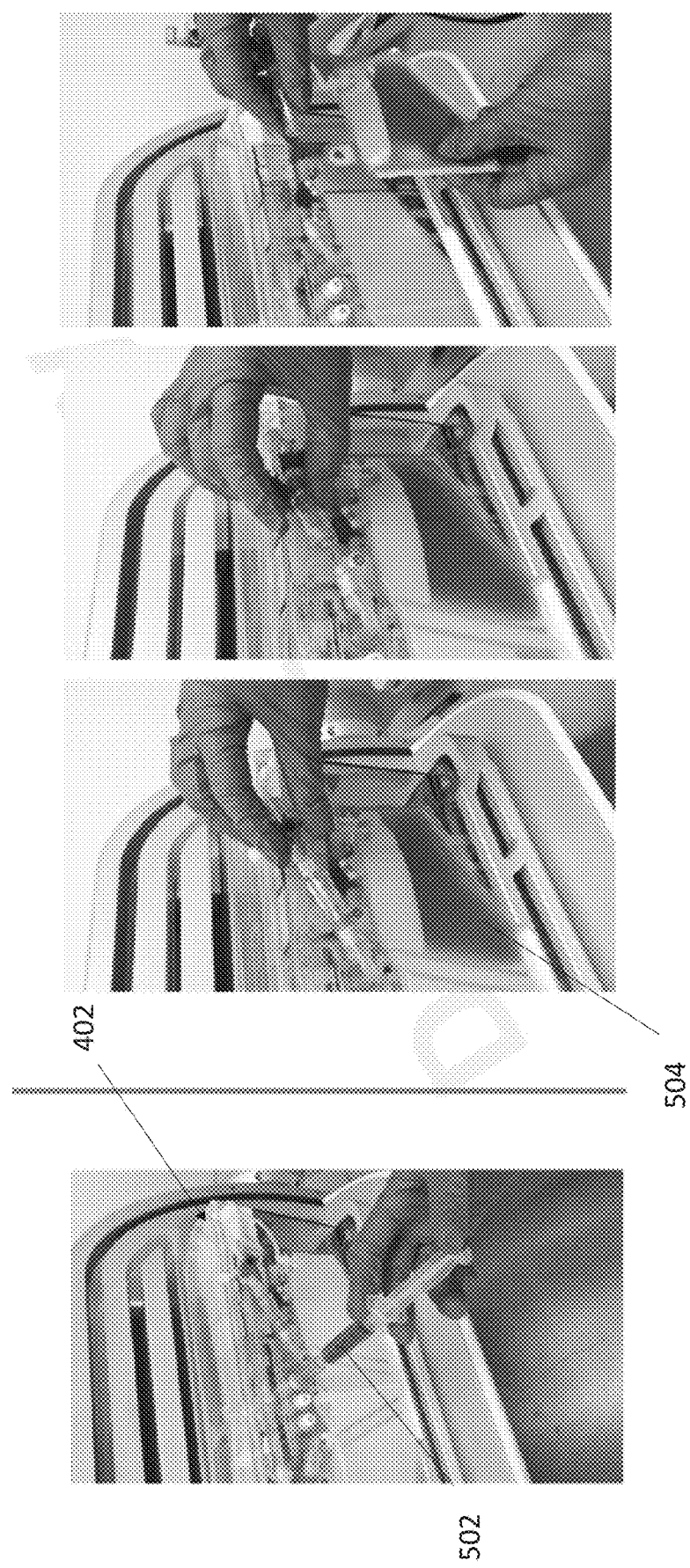
FIG. 5 shows the use of a syringe and a bag to sample from a cassette of an automated cell engineering system.

FIG. 5 shows a method for accessing the cells of an automated cell engineering system, including the methods described herein for producing various cell therapies. As indicated, a cassette 402, in which the various processes (transduction, expansion, etc.) are being carried out can be attached to a syringe 502. This syringe can be used to draw a sample of the cells during any stage of the process (e.g., during or after an one of the activating, transducing, expanding, and/or harvesting). This sample can then be used to analyze for the various molecular characteristics described herein. Also shown in FIG. 5 is a bag 504 which can be connected to the cassette if a larger cellular sample is desired or required.

Various optimizing methods are described herein and can include one or more of increasing or decreasing a flow rate of cell media, increasing or decreasing oxygen concentration, increasing or decreasing carbon dioxide concentration, increasing or decrease a glucose level, increasing or decreasing the temperature of a cell expansion, increasing or decreasing the pH of a cell media, modifying a cell transduction procedure, modifying a vector for use in a transduction procedure, and modifying a cell isolation procedure.

For example, if the molecular characteristics of the cell culture demonstrate that the culture will not achieve the necessary growth for a desired cell culture size, the cell engineering system can automatically increase the oxygen level of the cell culture by, e.g., introducing oxygenated cell culture media, by replacing the cell culture media with oxygenated cell culture media, or by flowing the cell culture media through an oxygenation component (i.e., a silicone tubing).

In another example, if the molecular characteristics indicate that the cell culture is growing too rapidly (e.g., possible overcrowding of the cells may lead to undesirable characteristics), the cell engineering system can automatically decrease the temperature of the cell culture to maintain a steady growth rate (or exponential growth rate, as desired) of the cells. In still further embodiments, based upon the analyzed molecular characteristics, the cell engineering system can automatically adjust the schedule of cell feeding (i.e., providing fresh media and/or nutrients to the cell culture) based on molecular characteristics.

In further embodiments, provided herein is a method for assessing and optimizing cellular quality of a chimeric antigen receptor T (CAR T) cell culture. The method suitably includes determining one or more molecular characteristics of a pre-modified T-cell culture, optimizing one or more parameters of an automated cell engineering system to alter one the one or more molecular characteristics of the pre-modified T-cell culture, activating the pre-modified T-cell culture with an activation reagent to produce an activated T-cell culture, transducing the activated T-cell culture with a vector encoding a chimeric antigen receptor, to produce a CAR T-cell culture, expanding the CAR T-cell culture, concentrating the expanded CAR T-cell culture and harvesting the concentrated CAR-T cell culture.

Suitably, the methods include determining the one or more molecular characteristics of the CAR T-cell culture during or after any one the steps of activating, transducing, expanding, concentrating or harvesting; and optimizing one or more parameters of any one of these steps to alter the one or more molecular characteristics of the CAR T-cell culture.

As described herein, suitably the one or more molecular characteristics include T-cell activation, metabolism, exhaustion, and T-cell receptor diversity. In exemplary embodiments, the one or more molecular characteristics include a gene expression, a protein expression, an mRNA expression, and a copy number variation.

As described herein with regard to a CAR T characterization panel, suitably the methods include the determination of at least about 500 gene expressions, suitably at least about 700 gene expressions, including where about 700-800 gene expressions are determined (including about 750, 760, 770, 780, 790 or 800 gene expressions).

As described herein, the optimizing of the automated process suitably includes one or more of increasing or decreasing a flow rate of cell media, increasing or decreasing oxygen concentration, increasing or decreasing carbon dioxide concentration, increasing or decrease a glucose level, increasing or decreasing the temperature of a cell expansion, increasing or decreasing the pH of a cell media, modifying a cell transduction procedure, modifying a vector for use in a transduction procedure, and modifying a cell isolation procedure.

The methods described herein, suitably are optimized so as to produce at least about 100 million viable CAR T-cells, including at least about 2 billion viable CAR T-cells.

Exemplary starting the T-cell cultures as described herein suitably include peripheral blood mononuclear cells and/or purified T-cells.

In exemplary embodiments, the T-cell culture comprises at least one accessory cell, which can be a monocyte or a monocyte-derived cell.

Suitably, the accessory cell comprises antigens for a T-cell receptor, including CD28, CD40, CD2, CD40L and/or ICOS.

As described herein, in embodiments, the activation reagent comprises an antibody or a dendritic cell. Suitably, the antibody is immobilized on a surface. This surface includes a surface of a bead. Suitably, the antibody is a soluble antibody, including at least one of an anti-CD3 antibody and an anti-CD28 antibody.

In exemplary embodiments, the transducing comprises viral infection, electroporation, membrane disruption, or combinations thereof.

In suitable embodiments, the vector used in the transduction is a lentiviral vector or a retrovirus.

Exemplary Process Flow for Assessing and Optimizing CAR T Production

Healthy donors and patient leukapheresis are used to manufacture CAR-T cells in an automated cell engineering system.

At multiple points throughout the cell therapy manufacturing, cells samples are taken and characterized by a CAR-T cell panel.

The data from all tests are analyzed to continually improve the detection panel (potential detection panel changes) and generate knowledge to understand how to translate cellular characteristics into avenues allowing further manufacturing process optimization.

Through collaboration with medical centers, a database can be generated to gain insight on how clinical outcomes are linked to cellular characteristics along with improved manufacturing processes with the aim to improve clinical efficacy and reduce treatment adverse events.

An improved CAR-T cell panel combined with translating cellular characteristics to optimize automated manufacturing processes will provide an analytic package which can be offered.

The following sections provide descriptions of the methods used in the automated cell engineering systems for production of CAR T cells.

Activation of T Cells. In some embodiments, an immune cell culture produced by the methods described herein is a CAR T cell culture. CAR T cells can be activated to form an activated T cell culture. In vivo, antigen-presenting cells (APCs), such as dendritic cells, act as the stimulus for T cell activation through the interaction of the T Cell Receptor (TCR) with the APC major histone compatibility complex (MHC). TCR associates with CD3, a T cell co-receptor that helps to activate both cytotoxic T cells (e.g., CD8+ naïve T cells) and T helper cells (e.g., CD4+ naïve T cells). In general, T cell activation follows a two-signal model, requiring stimulation of the TCR/CD3 complex as well as a co-stimulatory receptor. Activation of T cells is further described in, e.g., Kochenderfer 2015; Kalos 2011.

Without the co-stimulatory signal, the cells are susceptible to anergy and become non-responsive. Thus, T cell co-stimulation may be important for T cell proliferation, differentiation, and survival. Non-limiting examples of co-stimulatory molecules for T cells include CD28, which is a receptor for CD80 and CD86 on the membrane of APC; and CD278 or ICOS (Inducible T-cell COStimulator), which is a CD28 superfamily molecule expressed on activated T cells that interacts with ICOS-L. Thus, in some embodiments, the co-stimulatory molecule is CD28. In other embodiments, the co-stimulatory molecule is ICOS. In vivo, the co-stimulatory signal can be provided by the B7 molecules on the APC, which bind to the CD28 receptor on T cells. B7 is a peripheral transmembrane protein found on activated APCs that can interact with CD28 or CD152 surface proteins on a T cell to produce a co-stimulatory signal. Thus, in some embodiments, the co-stimulatory molecule is B7. Co-stimulatory receptors are further described in, e.g., Lafferty 1975; Harding 1992; Clavreul 2000; Charron 2015; Fathman 2007; Greenwald 2005. Co-stimulation is further described in, e.g., Carpenter 2000; Andris 2004. B7 molecules are further described in, e.g., Fleischer 1996; Schwartz 2003.

Various methods of activation are utilized in vitro to simulate T cell activation. In embodiments, a T cell culture is activated with an activation reagent. In further embodiments, the activation reagent is an antigen-presenting cell (APC). In still further embodiments, the activation reagent is a dendritic cell. Dendritic cells are APCs that process antigen and present it on the cell surface to T cells. In some embodiments, the activation reagent is co-cultured with the T cell culture. Co-culturing may require separate purification and culturing of a second cell type, which may increase labor requirements and sources of variability. Thus, in some embodiments, alternative activation methods are used.

In some embodiments, the activation reagent is an antibody. In some embodiments, the cell culture is activated with an antibody bound to a surface, including a polymer surface, including a beads. In further embodiments, the one or more antibodies is an anti-CD3 and/or anti-CD28 antibody. For example, the beads may be magnetic beads such as, e.g., DYNABEADS®, coated with anti-CD3 and anti-CD28. The anti-CD3 and anti-CD28 beads can suitably provide the stimulatory signals to support T cell activation. See, e.g., Riddell 1990; Trickett 2003.

In other embodiments, the cell culture is activated with a soluble antibody. In further embodiments, the soluble antibody is a soluble anti-CD3 antibody. OKT3 is a murine monoclonal antibody of the immunoglobulin IgG2a isotype and targets CD3. Thus, in some embodiments, the soluble anti-CD3 antibody is OKT3. OKT3 is further described in, e.g., Dudley 2003; Manger 1985; Ceuppens 1985; Van Wauwe 1980; Norman 1995.

In some embodiments, the co-stimulatory signal for T cell activation is provided by accessory cells. Accessory cells may include, for example, a Fc receptor, which enables cross-linking of the CD3 antibody with the TCR/CD3 complex on the T cell. In some embodiments, the cell culture is a mixed population of peripheral blood mononuclear cells (PBMCs). PBMC may include accessory cells capable of supporting T cell activation. For example, CD28 co-stimulatory signals can be provided by the B7 molecules present on monocytes in the PBMC. Accordingly, in some embodiments, the accessory cells include a monocyte or a monocyte-derived cell (e.g., a dendritic cell). In additional embodiments, the accessory cells include B7, CD28, and/or ICOS. Accessory cells are further described in, e.g., Wolf 1994; Chai 1997; Verwilghen 1991; Schwartz 1990; Ju 2003; Baroja 1989; Austyn 1987; Tax 1983.

As described herein, the activation reagent may determine the phenotype of the CAR T cells produced, allowing for the promotion of a desired phenotype. In some embodiments, the activation reagent determines the ratio of T cell subsets, i.e., CD4+ helper T cells and CD8+ cytotoxic T cells. The cytotoxic CD8+ T cells are typically responsible for killing cancer cells (i.e., the anti-tumor response), cells that are infected (e.g., with viruses), or cells that are damaged in other ways. CD4+ T cells typically produce cytokines and help to modulate the immune response, and in some cases may support cell lysis. CD4+ cells activate APCs, which then primes naïve CD8+ T cells for the anti-tumor response. Accordingly, in embodiments, the methods of the present disclosure further include producing CAR T cells of a pre-defined phenotype (i.e., promoting cells of a desired phenotype). The pre-defined phenotype may be, for example, a pre-defined ratio of CD8+ cells to CD4+ cells. In some embodiments, the ratio of CD8+ cells to CD4+ cells in a population of CAR T cells is about 1:1, about 0.25:1, or about 0.5:1. In other embodiments, the ratio of CD8+ cells to CD4+ cells in a population of CAR T cells is about 2:1, about 3:1, about 4:1, or about 5:1.

Methods in which a pre-defined phenotype are produced suitably include determining one or more molecular characteristics, i.e., the levels of CD8 and CD4, and are optimized by either selecting for such cells, or modifying the production parameters to push generation of such cells.

In embodiments, the activation reagent is removed from the activated T cell culture after the activation step. The activation reagent, e.g., an anti-CD3 antibody and/or an anti-CD28 antibody may be present in the cell culture media. Thus, in some embodiments, the cell culture media containing the activation reagent, e.g., an anti-CD3 antibody and/or an anti-CD28 antibody, is removed from the activated T cell culture after the activation step. In some embodiments, removal of the activation reagent includes removing a soluble antibody. For example, the soluble antibody can be removed by exchanging the cell culture media. The soluble antibody can also be removed by affinity methods specific for the soluble antibody. In other embodiments, removal of the activation reagent includes removing the bead containing the antibody. Bead removal can include, for example, filtering the beads or removal by a magnet.

Transduction of Activated T Cells. In some embodiments, the genetically modified immune cell culture is an activated T cell culture that is transduced with a vector encoding a chimeric antigen receptor to produce a transduced T cell culture. In some embodiments, the transduction includes viral infection, transposons, mRNA transfection, electroporation, or combinations thereof. In some embodiments, the transduction includes electroporation. Accordingly, in embodiments, the cell engineering system includes an electroporation system or electroporation unit. In additional embodiments, the transduction includes viral infection. The vector may be a viral vector, such as, for example, a lentiviral vector, a gammaretroviral vector, an adeno-associated viral vector, or an adenoviral vector. In embodiments, the transduction includes introducing a viral vector into the activated T cells of the cell culture. In additional embodiments, the vector is delivered as a viral particle.

In some embodiments, the transduction step includes transducing the activated T cells with a lentiviral vector, wherein the lentiviral vector is introduced at a multiplicity of infection (MOI) of about 0.5 to about 50, about 0.5 to about 30, or about 0.5 to about 20. In some embodiments, the lentiviral vector is introduced at a MOI of about 0.5 to about 8. In some embodiments, the lentiviral vector is introduced at a MOI of about 0.5 to about 6. In some embodiments, the lentiviral vector is introduced at a MOI of about 0.5 to about 4. In some embodiments, the lentiviral vector is introduced at a MOI of about 0.5 to about 2. In some embodiments, the lentiviral vector is introduced at a MOI of about 0.6 to about 1.5. In some embodiments, the lentiviral vector is introduced at a MOI of about 0.7 to about 1.3. In some embodiments, the lentiviral vector is introduced at a MOI of about 0.8 to about 1.1. In some embodiments, the lentiviral vector is introduced at a MOI of about 0.5, about 0.6, about 0.7, about 0.8, about 0.9, about 1, about 1.1, about 1.2, about 1.3, about 1.4, about 1.5, about 1.6, about 1.7, about 1.8, about 1.9, or about 2.

In some embodiments, after the activation step, the cell culture media from the T cell culture is removed, and the media is then mixed with the vector (e.g., lentiviral vector) and distributed uniformly to the cells. In some embodiments, the removed cell culture media is used to dilute and uniformly deliver the vector to the activated T cell culture. Uniform distribution and consequent homogeneous exposure of the vector (e.g., lentiviral vector) in the T cell culture improves transduction efficiency. In some embodiments, the volume of the cell culture is reduced after activation, and prior to addition of the vector. Volume reduction may enable a higher degree of cell-vector contact. In some embodiments, the activated T cell culture is substantially undisturbed during the transduction. In some embodiments, the cell culture is substantially undisturbed during the activation and transduction steps, i.e., the cells remain generally in the same area of the chamber (e.g., the bottom of the cell culture chamber) while the activation reagent or the vector is being provided to the cells. This may facilitate uniform distribution and homogeneous exposure of the activation reagent and/or vector to the cells, and thus may improve the activation and/or transduction efficiency.

Expansion of Transduced T Cells. In some embodiments, the transduced T cell culture (or other cell therapy or immune cell culture) is expanded to a pre-defined culture size (i.e., number of cells). The pre-defined culture size may include a sufficient number of cells suitable for clinical use, i.e., transfusion into a patient, research and development work, etc. In some embodiments, a clinical or therapeutic dose of CAR T cells for administration to a patient is about $10^5$ cells, about $10^6$ cells, about $10^7$ cells, about $10^8$ cells, about $10^9$ cells, or about $10^{10}$ cells. In some embodiments, the method produces at least 1, at least 2, at least 3, at least 4, at least 5, at least 10, at least 15, at least 20, at least 25, at least 30, at least 35, at least 40, at least 45, at least 50, at least 60, at least 70, at least 80, at least 90, or at least 100 clinical doses of CAR T cells. In some embodiments, the transduced T cell culture is expanded to a total volume of from about 0.1 L to about 5 L, from about 0.1 L to about 2 L, or from about 0.2 L to about 2 L. In some embodiments, the transduced T cell culture is expanded to a total volume of about 0.1 L, about 0.2 L, about 0.3 L, about 0.4 L, about 0.5 L, about 0.6 L, about 0.7 L, about 0.8 L, about 0.9 L or about 1.0 L. The volume can also be varied through the process, as required based on the stage of the cell production process. In some embodiments, the pre-defined culture size is input by a user of the cell engineering system. The user may input the pre-defined culture size as a desired cell count to be produced (e.g., $10^{10}$ CAR T cells), or, the pre-defined culture size may be input as a desired number of clinical or therapeutic doses to be produced (e.g., 10 clinical or therapeutic doses of CAR T cells). In embodiments, the number of CAR T cells produced by the methods described herein is at least about 100 million (i.e., $1*10^6$) cells, or at least about 300 million, at least about 500 million, at least about 600 million, at least about 700 million, at least about 800 million, at least about 900 million, at least about 1 billion (i.e., $1*10^9$), at least about 1.1 billion, at least about 1.2 billion, at least about 1.3 billion, at least about 1.4 billion, at least about 1.5 billion, at least about 1.6 billion, at least about 1.7 billion, at least about 1.8 billion, at least about 1.9 billion, at least about 2 billion (i.e., $2*10^9$) cells, including at least about 2.1 billion, at least about 2.2 billion, at least about 2.3 billion, at least about 2.4 billion, at least about 2.5 billion, at least about 2.6 billion, at least about 2.7 billion, at least about 2.8 billion, at least about 2.9 billion, or at least about 3.0 billion CAR T cells.

In some embodiments, the expanding of the transduced T cell culture includes at least one round of feeding, washing, monitoring, and selecting of the transduced T cell culture. Feeding the cell culture may include supplementing the cell culture with media and/or additional nutrients. Washing the cell culture may include removing spent media (i.e., media that is depleted of nutrients and/or contains cellular waste products) and replenishing the cell culture with fresh media. Monitoring the cell culture may include monitoring the temperature, pH, glucose, oxygen level, carbon dioxide level, and/or optical density of the cell culture. Selecting the cell culture may include selecting the cells with the desired characteristics such as, e.g., viability, type, and/or morphology, and removing cells that do not have the desired characteristics. In some embodiments, the cell engineering system is configured to perform several rounds of the feeding, washing, monitoring, and/or selecting of the transduced T cell culture to achieve the pre-defined culture size. In some embodiments, the cell engineering system performs at least 2, at least 3, at least 4, at least 5, at least 6, at least 7, at least 8, at least 9, at least 10, at least 15, at least 20, at least 25, at least 30, at least 35, at least 40, at least 45, at least 50, or at least 100 rounds of the feeding, washing, monitoring, and/or selecting of the transduced T cell culture to achieve the pre-defined culture size.

In embodiments, one or more of the feeding, washing and monitoring can be removed, or the order of the events can be changed depending on the desired cellular phenotype or number of cells, etc.

In embodiments, the monitoring includes monitoring with a temperature sensor, a pH sensor, a glucose sensor, an oxygen sensor, a carbon dioxide sensor, and/or an optical density sensor. Accordingly, in some embodiments, the cell engineering system includes one or more of a temperature sensor, a pH sensor, a glucose sensor, an oxygen sensor, a carbon dioxide sensor, and/or an optical density sensor. In additional embodiments, the cell engineering system is configured to adjust the temperature, pH, glucose, oxygen level, carbon dioxide level, and/or optical density of the cell culture, based on the pre-defined culture size. For example, if the cell engineering system detects that the current oxygen level of the cell culture is too low to achieve the necessary growth for a desired cell culture size, the cell engineering system will automatically increase the oxygen level of the cell culture by, e.g., introducing oxygenated cell culture media, by replacing the cell culture media with oxygenated cell culture media, or by flowing the cell culture media through an oxygenation component (i.e., a silicone tubing). In another example, if the cell engineering system detects that the current temperature of the cell culture is too high and that the cells are growing too rapidly (e.g., possible overcrowding of the cells may lead to undesirable characteristics), the cell engineering system will automatically decrease the temperature of the cell culture to maintain a steady growth rate (or exponential growth rate, as desired) of the cells. In still further embodiments, the cell engineering system automatically adjusts the schedule of cell feeding (i.e., providing fresh media and/or nutrients to the cell culture) based on the cell growth rate and/or cell count, or other monitored factors, such as pH, oxygen, glucose, etc. The cell engineering system may be configured to store media (and other reagents, such as wash solutions, etc.) in a low-temperature chamber (e.g., 4° C. or −20° C.), and to warm the media in a room temperature chamber or a high-temperature chamber (e.g., 25° C. or 37° C., respectively) before introducing the warmed media to the cell culture.

In embodiments, the washing includes washing the cells by filtration or sedimentation. In embodiments, the selecting includes mixing the cell culture with one or more selection reagents. The selection reagent may be a bead, e.g., a magnetic bead, that is specific for the desired cell type, and the cells bound to the beads are then separated from non-bound cells, e.g., by passing through a magnetic chamber. For example, the selection bead includes an antibody specific for a desired cell type, e.g., an anti-CD8 antibody or an anti-CD4 antibody. Selection can also be performed by filtration to remove or select certain cell types based on size. Cell selection by plastic-adhesion (i.e. cells can start in one chamber, the unwanted cells stick to the surface and then the desired cells, that are still in suspension, are moved to another chamber), can also be utilized.

Concentration of the Expanded Culture. In some embodiments, the expanded T cell culture (or other cell therapy include other immune cell cultures) is concentrated to a pre-defined concentration. The pre-defined concentration is a volume that can be suitably infused into a patient. For example, the expanded T cell culture can be concentrated to about 1 ml, about 2 ml, about 5 ml, about 10 ml, about 15 ml, about 20 ml, about 25 ml, about 30 ml, about 35 ml, about 40 ml, about 45 ml, about 50 ml, about 55 ml, about 60 ml, about 65 ml, about 70 ml, about 75 ml, about 80 ml, about 85 ml, about 90 ml, about 95 ml, or about 100 ml. In some embodiments, the concentration is performed by centrifugation. In some embodiments, the concentration is performed by filtration. In some embodiments, the filtration is ultrafiltration and/or diafiltration. In some embodiments, the pre-defined concentration is input by a user of the cell engineering system. In other embodiments, the pre-defined concentration is determined by the cell engineering system, based on a different parameter input by the user, for example, the number or volume of clinical or therapeutic doses to be produced; or the number of cells to be produced. In some embodiments, the cell engineering system automatically adjusts the volume or number of clinical or therapeutic doses produced, based on the input parameters. In some embodiments, the cell engineering system automatically adjusts parameters of the centrifugation (e.g., speed, duration of centrifuging) or filtration (e.g., filter size, volume, duration) based on the pre-defined concentration.

Sedimentation based on the port position and design of the chamber can also be utilized. That is, the fluid volume can be reduced in the chamber to approximately 0.5 mL without removing the cells.

CAR T Cell Culture Harvest. In some embodiments, the concentrated T cell culture (or other cell therapy including other immune cell cultures) is harvested, suitably to produce a chimeric antigen receptor (CAR) T cell culture. In some embodiments, the harvesting includes agitation, fluid flow, and washing of the CAR T cells. In some embodiments, the harvesting includes separation of the cells from undesired products, which include, e.g., cellular waste products, selection reagents such as beads (e.g., beads containing antibodies and/or beads used for separation of cells), or excess viral vectors. In some embodiments, the harvesting includes uniform distribution of the CAR T cells into one or more flasks, vials or vessels. In some embodiments, the harvesting includes resuspending the CAR T cells in a formulation reagent, e.g., a solution that stabilizes the CAR T cells for long-term storage. In some embodiments, the harvesting includes cryopreservation of the CAR T cells.

Further Downstream Processes. In some embodiments, the CAR T cells (or other cell therapy including other immune cells) undergo further downstream processing prior to therapeutic use in a patient. For example, the CAR T cells may be filtered by sterile filtration to remove potential viral particle remnants. After sterile filtration, the CAR T cells may undergo at least one more concentration step before packaged in one or more vials, flasks, vessels, or containers. The packaged CAR T cells may be subjected to quality assessment and/or quality control testing as described herein. In some embodiments, the CAR T cells undergo minimal downstream processing prior to administration to a patient. For example, in some embodiments, harvested CAR T cells are not cryopreserved but transferred to the patient within a short time period after harvest. Avoiding the cryopreservation step may increase the viability of the cells.

Additional Exemplary Embodiments

Embodiment 1 is a method for assessing and optimizing cellular quality of a cell-based therapy, comprising: determining one or more molecular characteristics of a pre-modified cell culture; genetically modifying the cell culture via an automated cell engineering system; determining the one or more molecular characteristics of the modified cell culture during and after the genetically modifying; and optimizing one or more parameters of the automated cell engineering system to alter the one or more molecular characteristics of the modified cell culture.

Embodiment 2 includes the method of embodiment 1, wherein the one or more molecular characteristics are selected from the group consisting of a gene expression, a protein expression, an mRNA expression, and a copy number variation.

Embodiment 3 includes the method of embodiment 1 or embodiment 2, wherein the cell culture is an immune cell culture, a natural killer cell culture, and a cell culture for a neurodegenerative therapy.

Embodiment 4 includes the method of embodiment 3, wherein the immune cell culture is a T-cell culture.

Embodiment 5 includes the method of embodiment 4, wherein T cell culture is a chimeric antigen receptor T (CAR T) cell culture.

Embodiment 6 includes the method of embodiment 5, wherein the one or more molecular characteristics include T-cell activation, metabolism, exhaustion, and T-cell receptor diversity.

Embodiment 7 includes the method of any one of embodiments 1-6, wherein the optimizing in (d) occurs before, during, and/or after the genetically modifying.

Embodiment 8 includes the method of any one of embodiments 1-7, wherein the optimizing includes one or more of increasing or decreasing a flow rate of cell media, increasing or decreasing oxygen concentration, increasing or decreasing carbon dioxide concentration, increasing or decreasing a glucose level, increasing or decreasing the temperature of a cell expansion, increasing or decreasing the pH of a cell media, modifying a cell transduction procedure, modifying a vector for use in a transduction procedure, and modifying a cell isolation procedure.

Embodiment 9 is a method for assessing and optimizing cellular quality of a cell-based therapy, comprising: determining one or more molecular characteristics of a pre-modified cell culture; optimizing one or more parameters of an automated cell engineering systems to alter one the one or more molecular characteristics of the pre-modified cell culture; activating the pre-modified cell culture with an activation reagent to produce an activated cell culture; transducing the activated immune cell culture with a vector, to produce a transduced cell culture; expanding the transduced cell culture; concentrating the expanded cell culture of (e); harvesting the concentrated cell culture of (f) to produce a genetically modified cell culture; determining the one or more molecular characteristics of the cell culture during or after any one of steps (c)-(g); and optimizing one or more parameters of any one of steps (c)-(g) to alter the one or more molecular characteristics of the cell culture.

Embodiment 10 includes the method of embodiment 9, wherein the one or more molecular characteristics are selected from the group consisting of a gene expression, a protein expression, an mRNA expression, and a copy number variation.

Embodiment 11 includes the method of embodiment 9 or embodiment 10, wherein the cell culture is an immune cell culture, a natural killer cell culture, and a cell culture for a neurodegenerative therapy.

Embodiment 12 includes the method of embodiment 11, wherein the immune cell culture is a T-cell culture.

Embodiment 13 includes the method of embodiment 12, wherein T-cell culture is a chimeric antigen receptor T (CAR T) cell culture.

Embodiment 14 includes the method of embodiment 13, wherein the one or more molecular characteristics include T-cell activation, metabolism, exhaustion, and T-cell receptor diversity.

Embodiment 15 includes the method of any one of embodiments 9-14, wherein the optimizing includes one or more of increasing or decreasing a flow rate of cell media, increasing or decreasing oxygen concentration, increasing or decreasing carbon dioxide concentration, increasing or decrease a glucose level, increasing or decreasing the temperature of a cell expansion, increasing or decreasing the pH of a cell media, modifying a cell transduction procedure, modifying a vector for use in a transduction procedure, and modifying a cell isolation procedure.

Embodiment 16 is a method for assessing and optimizing cellular quality of a chimeric antigen receptor T (CAR T) cell culture, comprising: determining one or more molecular characteristics of a pre-modified T-cell culture; optimizing one or more parameters of an automated cell engineering system to alter one the one or more molecular characteristics of the pre-modified T-cell culture; activating the pre-modified T-cell culture with an activation reagent to produce an activated T-cell culture; transducing the activated T-cell culture with a vector encoding a chimeric antigen receptor, to produce a CAR T-cell culture; expanding the CAR T-cell culture; concentrating the expanded CAR T-cell culture of (e); harvesting the concentrated CAR-T cell culture of (f); determining the one or more molecular characteristics of the CAR T-cell culture during or after any one of steps (c)-(g); and optimizing one or more parameters of any one of steps (c)-(g) to alter the one or more molecular characteristics of the CAR T-cell culture.

Embodiment 17 includes the method of embodiment 16, wherein the method produces at least about 100 million viable CAR T-cells Embodiment 18 includes the method of embodiment 16, wherein the method produces at least about 2 billion viable CAR T-cells Embodiment 19 includes the method of embodiment 16-19, wherein the T-cell culture comprises peripheral blood mononuclear cells and/or purified T-cells.

Embodiment 20 includes the method of any one of embodiments 16-19, wherein the T-cell culture comprises at least one accessory cell.

Embodiment 21 includes the method of embodiment 20, wherein the accessory cell comprises a monocyte or a monocyte-derived cell.

Embodiment 22 includes the method of embodiment 20, wherein the accessory cell comprises antigens for a T-cell receptor, including CD28, CD40, CD2, CD40L and/or ICOS.

Embodiment 23 includes the method of any one of embodiments 16-22, wherein the activation reagent comprises an antibody or a dendritic cell.

Embodiment 24 includes the method of embodiment 23, wherein the antibody is immobilized on a surface.

Embodiment 25 includes the method of embodiment 24, wherein the surface is a surface of a bead.

Embodiment 26 includes the method of embodiment 23, wherein the antibody is a soluble antibody.

Embodiment 27 includes the method of embodiment 23, wherein the antibody comprises at least one of an anti-CD3 antibody and an anti-CD28 antibody.

Embodiment 28 includes the method of any one of embodiments 16-27, wherein the transducing comprises viral infection, electroporation, membrane disruption, or combinations thereof.

Embodiment 29 includes the method of any one of embodiments 16-28, wherein the vector is a lentiviral vector or a retrovirus.

Embodiment 30 includes the method of any one of embodiments 16-29, wherein the one or more molecular characteristics include T-cell activation, metabolism, exhaustion, and T-cell receptor diversity.

Embodiment 31 includes the method of any one of embodiments 16-30, wherein the one or more molecular characteristics are selected from the group consisting of a gene expression, a protein expression, an mRNA expression, and a copy number variation.

Embodiment 32 includes the method of embodiment 31, wherein at least about 500 gene expressions are determined.

Embodiment 33 includes the method of embodiment 31, wherein at least about 700 gene expressions are determined.

Embodiment 34 includes the method of embodiment 31, wherein about 780 gene expressions are determined.

Embodiment 35 includes the method of any one of embodiments 16-34, wherein the optimizing includes one or more of increasing or decreasing a flow rate of cell media, increasing or decreasing oxygen concentration, increasing or decreasing carbon dioxide concentration, increasing or decrease a glucose level, increasing or decreasing the temperature of a cell expansion, increasing or decreasing the pH of a cell media, modifying a cell transduction procedure, modifying a vector for use in a transduction procedure, and modifying a cell isolation procedure.

Embodiment 36 is a method for assessing and optimizing cellular quality of a cell culture, comprising: determining one or more molecular characteristics of a pre-modified cell culture; genetically modifying the cell culture via an automated cell engineering system; determining the one or more molecular characteristics of the modified cell culture during and after the genetically modifying; and optimizing one or more parameters of the automated cell engineering system to alter the one or more molecular characteristics of the modified cell culture.

REFERENCES CITED

FDA, Regenerative Medicine Advanced Therapy Designation. (2017). Available at: fda.gov Wang, X. & Rivière, I. Clinical manufacturing of CAR T cells: foundation of a promising therapy. Mol. Ther.— Oncolytics 3, 16015 (2016).

Jones, S. D., McKee, S. & Levine, H. L. Emerging challenges in cell therapy manufacturing. BioProcess Int 10, S4-S7 (2012).

Trainor, N., Pietak, A. & Smith, T. Rethinking clinical delivery of adult stem cell therapies. Nat Biotech 32, 729-735 (2014).

Nilsson, C. et al. Optimal Blood Mononuclear Cell Isolation Procedures for Gamma Interferon Enzyme-Linked Immunospot Testing of Healthy Swedish and Tanzanian Subjects. Clin. Vaccine Immunol. 15, 585-589 (2008).

Bohnenkamp, H., Hilbert, U. & Noll, T. Bioprocess development for the cultivation of human T-lymphocytes in a clinical scale. Cytotechnology 38, 135-145 (2002).

Lu, F. et al. Automated dynamic fed-batch process and media optimization for high productivity cell culture process development. Biotechnol. Bioeng. 110, 191-205 (2013).

Hollyman, D. et al. Manufacturing validation of biologically functional T cells targeted to CD19 antigen for autologous adoptive cell therapy. J. Immunother. 32, 169-180 (2009).

FDA, Sepax Cell Separation System and single use kits. (2011). Available at: fda.gov Wegener, C. Cell Washing with the LOVO Cell Processing System. BioProcess Int Industry Y, p 78 (2014).

Trickett, A. & Kwan, Y. L. T cell stimulation and expansion using anti-CD3/CD28 beads. J. Immunol. Methods 275, 251-255 (2003).

Hasegawa, K. et al. In vitro stimulation of CD8 and CD4 T cells by dendritic cells loaded with a complex of cholesterol-bearing hydrophobized pullulan and NY-ESO-1 protein: Identification of a new HLA-DR15-binding CD4 T-cell epitope. Clin. Cancer Res. 12, 1921-1927 (2006).

Odeleye, A. O. O., Marsh, D. T. J., Osborne, M. D., Lye, G. J. & Micheletti, M. On the fluid dynamics of a laboratory scale single-use stirred bioreactor. Chem. Eng. Sci. 111, 299-312 (2014).

Grishagin, I. V. Automatic cell counting with ImageJ. Anal. Biochem. 473, 63-65 (2015).

Levine, B. L., Miskin, J., Wonnacott, K. & Keir, C. Global Manufacturing of CAR T Cell Therapy. Mol. Ther. Methods Clin. Dev. 4, 92-101 (2017).

Locke, F. L. et al. Abstract CT019: Primary results from ZUMA-1: a pivotal trial of axicabtagene ciloleucel (axi-cel; KTE-C19) in patients with refractory aggressive non-Hodgkin lymphoma (NHL). Cancer Res. 77, CT019 LP-CT019 (2017).

Lu Y C, Parker L L, Lu T, Zheng Z, Toomey M A, White D E, Yao X, Li Y F, Robbins P F, Feldman S A, van der Bruggen P, Klebanoff C A, Goff S L, Sherry M S, Kammula U S, Yang J C, Rosenberg S A. Treatment of patients with metastatic cancer using a major histocompatibility complex class II-restricted T-cell receptor targeting the cancer germline antigen MAGE-A3. Journal of Clinical Oncology (2017) 35:29, 3322-3329.

FDA, Available online at: fda.gov

Berdeja J G, Lin Y, Raje N S, Siegel D S D, Munshi N C, Liedtke M, Jagannath S, Maus M V, Turka A, Lam L P, Hege K, Morgan R, Quigley M T, Kochenderfer J. First-in-human multicenter study of bb2121 anti-BCMA CAR T-cell therapy for relapsed/refractory multiple myeloma: Updated results. Journal of Clinical Oncology 2017 35:15_suppl, 3010-3010

Kebriaei P, Singh H, Huls M H, Figiola M J, Bassett R, Olivares S, Jena B, Dawson M J, Kumaresan P R, Su S, Maiti S, Dai J, Moriarity B, Forget M A, Senyukov V, Orozco A, Liu T, McCarty J, Jackson R N, Moyes J S, Rondon G, Qazilbash M, Ciurea S, Alousi A, Nieto Y, Rezvani K, Marin D, Popat U, Hosing C, Shpall E J, Kantarjian H, Keating M, Wierda W, Do K A, Largaespada D A, Lee D A, Hackett P B, Champlin R E, Cooper L J N. Phase I trials using Sleeping Beauty to generate CD19-specific CAR T cells. J Clin Invest. 2016 Sep. 1; 126(9): 3363-3376.

Morrissey J B, Shi Y, Trainor N. End-to-end cell therapy automation: an immunotherapy case study. BioProcess International (2017) 10-18.

Lafferty K J, Cunningham A J A. New analysis of allogeneic interactions. J. Immunol. (1975) 112: 436-437.

Harding F, McArthur J, Gross J, Raulet D, Allison J. CD28-mediated signalling co-stimulates murine T cells and prevents induction of anergy in T-cell clones (1992) Nature 356: 607-609.

Clavreul A, Fisson S, D'hellencourt C L, Couez D. Interelationship between CD3 and CD28 pathways in a murine T cell thymoma. Mol Immunol. (2000) 37(10): 571-7.

Charron L, Doctrinal A, Choileain S N, Astier A L. Monocyte: T cell interaction regulates human T cell activation through a CD28/CD46 crosstalk. Immunol Cell Biol. (2015) 93(9): 796-803.

Fathman C G 1, Lineberry N B. Molecular mechanisms of CD4+ T-cell anergy. Nat Rev Immunol. (2007) 7(8): 599-609.

Greenwald R J, Freeman G J, Sharpe A H. The B7 family revisited. Annual Review of Immunology (2005) 23(1): 515-548.

Kochenderfer J N, Dudley M E, Kassim S H, et al. Chemotherapy-refractory diffuse large B-cell lymphoma and indolent B-cell malignancies can be effectively treated with autologous T cells expressing an anti-CD19 chimeric antigen receptor. Journal of Clinical Oncology (2015); 33(6): 540-549.

Kalos M, Levine B L, Porter D L, et al. T Cells with Chimeric Antigen Receptors Have Potent Antitumor Effects and Can Establish Memory in Patients with Advanced Leukemia. Science Translational Medicine (2011) 3(95): 95ra73.

Riddell S R, Greenberg P D. The use of anti-CD3 and anti-CD28 monoclonal antibodies to clone and expand human antigen-specific T cells. J Immunol Methods (1990) April 17; 128(2): 189-201.

Trickett A, Kwan Y L. T cell stimulation and expansion using anti-CD3/CD28 beads. Journal of Immunological Methods. 275 (2003) 251-255.

Dudley M E, Wunderlich J R, Shelton T E, Even J, Rosenberg S A. Generation of Tumor-Infiltrating Lymphocyte Cultures for Use in Adoptive Transfer Therapy for Melanoma Patients. Journal of immunotherapy (2003) 26(4): 332-342.

Dudley M E, Wunderlich J R, Shelton T E, Even J, Rosenberg S A. Generation of tumor-infiltrating lymphocyte cultures for use in adoptive transfer therapy for melanoma patients. J Immunother. (2003) 26(4): 332-342.

Manger B, Weiss A, Weyand C, Goronzy J, Stobo J D. T cell activation: differences in the signals required for IL 2 production by nonactivated and activated T cells. J Immunother. (1985) 135 (6) 3669-3673.

Ceuppens J, Bloemmen F J, Van Wauwe J P. T cell unresponsiveness to the mitogenic activity of OKT3 antibody results from a deficiency of monocyte Fc gamma receptors for murine IgG2a and inability to cross-link the T3-Ti complex. J Immunol (1985) 135 (6) 3882-3886.

Van Wauwe J P, De Mey J R, Goossens J G. OKT3: a monoclonal anti-human T lymphocyte antibody with potent mitogenic properties. J Immunol. (1980) 124(6): 2708-13.

Carpenter P A, Pavlovic S, Tso J Y, Press O W, Gooley T, Yu X Z, Anasetti C. Non-Fc receptor-binding humanized anti-CD3 antibodies induce apoptosis of activated human T cells. J Immunol (2000) 165 (11) 6205-6213.

Andris F, Denanglaire S, de Mattia F, Urbain J, Leo O. Naive T cells are resistant to anergy induction by anti-CD3 antibodies. J of Immunology (2004) 173 (5) 3201-3208.

Wolf H, Müller Y, Salmen S, Wilmanns W, Jung G. Induction of anergy in resting human T lymphocytes by immobilized anti-CD3 antibodies. Eur J Immunol. (1994) 24(6): 1410-1417.

Chai J G, Lechler R I. Immobilized anti-CD3 mAb induces anergy in murine naive and memory CD4+ T cells in vitro. Int Immunol. (1997) 9(7): 935-944.

Verwilghen J, Baroja M L, Van Vaeck F, Van Damme J, Ceuppens J L. Differences in the stimulating capacity of immobilized anti-CD3 monoclonal antibodies: variable dependence on interleukin-1 as a helper signal for T-cell activation. Immunology (1991) 72(2): 269-276.

Schwartz R H. A cell-culture model for lymphocyte-T clonal anergy. Science (1990) 248: 1349-1356.

Ju S W, Ju S G, Wang F M, Gu Z J, Qiu Y H, Yu G H, Ma H B, Zhang X G. A functional anti-human 4-1BB ligand monoclonal antibody that enhances proliferation of monocytes by reverse signaling of 4-1BBL. Hybridoma and Hybridomics. (2003) 22: 333-338.

Baroja M L, Lorre K, Van Vaeck F, Ceuppens J L. The anti-T cell monoclonal antibody 9.3 (anti-CD28) provides a helper signal and bypasses the need for accessory cells in T cell activation with immobilized anti-CD3 and mitogens. Cell Immunol. (1989) 120(1): 205-217.

Austyn J M, Smith K G, Morris P J. T cell activation by anti-CD3 antibodies: function of Fc receptors on B cell blasts, but not resting B cells, and CD18 on the responding T cells. Eur J Immunol. 1987 17(9): 1329-35.

Tax W J M, Willems H W, Reekers P P M, Capel P J A, Koene R A P. Polymorphism in mitogenic effect of IgG1 monoclonal antibodies against T3 antigen on human T cells. Nature (1983) 304: 445-447.

Fleischer J, Soeth E, Reiling N, Grage-Griebenow E, Flad H D, Ernst M. Differential expression and function of CD80 (B7-1) and CD86 (B7-2) on human peripheral blood monocytes. Immunology (1996) 89(4): 592-598.

Schwartz R H. T cell anergy. Annual Review Immunology (2003) 21: 305-34.

Feldmann A, Arndt C, Töpfer K, Stamova S, Krone F, Cartellieri M, Koristka S, Michalk I, Lindemann D, Schmitz M, Temme A, Bornhauser M, Ehninger G, Bachmann M. Novel humanized and highly efficient bispecific antibodies mediate killing of prostate stem cell antigen-expressing tumor cells by CD8+ and CD4+ T cells. J Immunol. (2012) 189(6): 3249-3259.

Reusch U, Duell J, Ellwanger K, Herbrecht C, Knackmuss S H, Fucek I, Eser M, McAleese F, Molkenthin V, Gall F L, et al. A tetravalent bispecific TandAb (CD19/CD3), AFM11, efficiently recruits T cells for the potent lysis of CD19(+) tumor cells. MAbs. (2015) 7: 584-604.

Church S E, Jensen S M, Antony P A, Restifo N P, Fox B A. Tumor-specific CD4+ T cells maintain effector and memory tumor-specific CD8+ T cells. Eur J Immunol. (2014) 44(1): 69-79.

Feldmann A, Arndt C, Töpfer K, Stamova S, Krone F, Cartellieri M, Koristka S, Michalk I, Lindemann D, Schmitz M, Temme A, Bornhauser M, Ehninger G, Bachmann M. Novel humanized and highly efficient bispecific antibodies mediate killing of prostate stem cell antigen-expressing tumor cells by CD8+ and CD4+ T cells. J Immunol. (2012) 189: 3249-3259.

Reusch U, Duell J, Ellwanger K, Herbrecht C, Knackmuss S H, Fucek I, Eser M, McAleese F, Molkenthin V, Gall F L, Topp M, Little M, Zhukovsky E A. A tetravalent bispecific TandAb (CD19/CD3), AFM11, efficiently recruits T cells for the potent lysis of CD19(+) tumor cells. (2015) 7:584-604.

Riddell S R, Sommermeyer D, Berger C, et al. Adoptive therapy with chimeric antigen receptor-modified T cells of defined subset composition. Cancer J. (2014) 20(2): 141-144.

Turtle C J, Hanafi L-A, Berger C, et al. CD19 CAR-T cells of defined CD4+:CD8+ composition in adult B cell ALL patients. The Journal of Clinical Investigation. (2016) 126(6): 2123-2138.

Locke F L, Neelapu S S, Bartlett N L, Siddiqi T, Siddiqi T, Chavez J C, Hosing C M, Ghobadi A, Budde L E, Bot A, Rossi J M, Jiang Y, Xue A X, Elias M, Aycock J, Wiezorek J, Go W Y. Phase 1 Results of ZUMA-1: A multicenter study of KTE-C19 anti-CD19 CART cell therapy in refractory aggressive lymphoma. Molecular Therapy (2017) 25(1): 285-295.

Trainor N, Pietak A, Smith T. Rethinking clinical delivery of adult stem cell therapies. Nature Biotech (2014) 729-735.

Mandavi B, Gottschalk U, Trainor N, Smith T. The hype, hope and reality of personalization. The Medicine Maker (2015) 38-41.

Yan M, Schwaederle M, Arguello D, Millis S Z, Gatalica Z, Kurzrock R. HER2 expression status in diverse cancers: review of results from 37,992 patients. Cancer Metastasis Review (2015) 34(1): 157-164.

Tuefferd M, Couturier J, Penault-Llorca F, Vincent-Salomon A, Broët P, Guastalla J P, Allouache D, Combe M, Weber B, Pujade-Lauraine E, Camilleri-Broët S. HER2 Status in Ovarian Carcinomas: A Multicenter GINECO Study of 320 Patients (2007) 2(11):e1138.

Lu T L, Pugach M, Somerville R, Rosenberg S A, Kochendefer J N, Better M, Feldman S A. A rapid cell expansion process for production of engineered autologous CAR-T cell therapies. Human Gene Therapy (2016) 27: 209-218.

Nociari M M, Shalev A, Benias P, Russo C. A novel one-step, highly sensitive fluorometric assay to evaluate cell-mediated cytotoxicity. J Immunol Methods (1998) 213(2): 157-167.

Romagnani S. Type 1 T helper and type 2 T helper cells: functions, regulation and role in protection and disease. Int J Clin Lab Res (1991) 21(2): 152-158.

Fleischer J, Soeth E, Reiling N, Grage-Griebenow E, Flad H D, Ernst M. Differential expression and function of CD80 (B7-1) and CD86 (B7-2) on human peripheral blood monocytes. Immunology (1996) 89(4): 592-598.

Laux I, Khoshnan A, Tindell C, Bae D, Zhu X M, June C H, Effros R B, Nel A. Response differences between human CD4+ and CD8+ T-cells during CD28 costimulation: Implications for immune cell-based therapies and studies related to the expansion of double-positive T-cells during aging. Clin Immunol. (2000) 96: 187-197.

Li Y, Kurlander R J. Comparison of anti-CD3 and anti-CD28-coated beads with soluble anti-CD3 for expanding human T cells: Differing impact on CD8 T cell phenotype and responsiveness to restimulation. J Transl Med. (2010) 8: 104.

Zhu Y W, Zhu G F, Luo L Q, Flies A S, Chen L P. CD137 stimulation delivers an antigen-independent growth signal for T lymphocytes with memory phenotype. Blood (2007) 109: 4882-4889.

Ledbetter J A, Imboden J B, Schieven G L, Grosmaire L S, Rabinovitch P S, Lindsten T, Thompson C B, June C H. CD28 Ligation in T-cell Activation: Evidence for Two Signal Transduction Pathways. Blood (1990) 75(7): 1531-1539.

Atkuri K R, Herzenberg L A, Herzenberg L A. Culturing at atmospheric oxygen levels impacts lymphocyte function. Proceedings of the National Academy of Sciences of the United States of America (2005) 102(10): 3756-3759.

Avgoustiniatos E S, Hering B J, Rozak P R, et al. Commercially Available Gas-Permeable Cell Culture Bags May Not Prevent Anoxia in Cultured or Shipped Islets. Transplantation proceedings. 2008; 40(2):395-400.

Hammill J A, VanSeggelen H, Nelsen C W, Denisova G F, Evelegh C, Tantalo D G M, Bassett J D, Bramson J L. Designed ankyrin repeat proteins are effective targeting elements for chimeric antigen receptors. Journal for ImmunoTherapy of Cancer (2015) 3:55.

VanSeggelen H, Tantalo D G M, Afsahi A, Hammill J A, Bramson J L. Chimeric antigen receptor-engineered T cells as oncolytic virus carriers. Molecular Therapy—Oncolytics (2015) 2, 150014.

It will be readily apparent to one of ordinary skill in the relevant arts that other suitable modifications and adaptations to the methods and applications described herein can be made without departing from the scope of any of the embodiments.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

All publications, patents and patent applications mentioned in this specification are herein incorporated by reference to the same extent as if each individual publication, patent or patent application was specifically and individually indicated to be incorporated by reference.

The invention claimed is:

1. A method for assessing and optimizing cellular quality of a cell-based therapy, comprising:
   (a) determining one or more molecular characteristics of a pre-modified cell culture;
   (b) genetically modifying the cell culture via an automated cell engineering system;
   (c) automatically determining via the automated cell engineering system the one or more molecular characteristics of the modified cell culture during and after the genetically modifying; and
   (d) automatically optimizing one or more parameters of the automated cell engineering system based on the automatically determined one or more molecular characteristics, by increasing or decreasing a flow rate of cell media, increasing or decreasing oxygen concentration, increasing or decreasing carbon dioxide concentration, increasing or decreasing a glucose level, increasing or decreasing a pH of cell media, and/or modifying a selection reagent used in a cell isolation procedure, to alter the one or more molecular characteristics of the modified cell culture.

2. The method of claim 1, wherein the one or more molecular characteristics are selected from the group consisting of a gene expression, a protein expression, an mRNA expression, and a copy number variation.

3. The method of claim 1, wherein the cell culture is selected from the group consisting of an immune cell culture, a natural killer cell culture, and a stem cell.

4. The method of claim 3, wherein the immune cell culture is a chimeric antigen receptor T (CAR T) cell culture.

5. The method of claim 4, wherein the one or more molecular characteristics include T-cell activation, metabolism, exhaustion, and T-cell receptor diversity.

6. The method of claim 1, further comprising automatically optimizing one or more parameters of the automated cell engineering system based on the determined one or more molecular characteristics of step (a) by modifying a selection of a cell transduction procedure and/or modifying a selection of a vector for use in a transduction procedure.

7. A method for assessing and optimizing cellular quality of a cell-based therapy, comprising:
   (a) determining one or more molecular characteristics of a pre-modified cell culture;
   (b) optimizing one or more parameters of an automated cell engineering systems to alter the one or more molecular characteristics of the pre-modified cell culture;
   (c) activating the pre-modified cell culture with an activation reagent to produce an activated cell culture;
   (d) transducing the activated cell culture with a vector, to produce a transduced cell culture;
   (e) expanding the transduced cell culture;
   (f) concentrating the expanded cell culture of (e);
   (g) harvesting the concentrated cell culture of (f) to produce a genetically modified cell culture;
   (h) automatically determining via the automated cell engineering system the one or more molecular characteristics of the cell culture selected from the group consisting of a gene expression, a protein expression, an mRNA expression, and a copy number variation during or after any one of steps (c)-(g); and
   (i) automatically optimizing one or more parameters based on the automatically determined one or more molecular characteristics of the cell culture, by increasing or decreasing a flow rate of cell media, increasing or decreasing oxygen concentration, increasing or decreasing carbon dioxide concentration, increasing or decreasing a glucose level, increasing or decreasing a pH of cell media, and/or modifying a selection reagent used in a cell isolation procedure to alter the one or more molecular characteristics of the cell culture.

8. The method of claim 7, wherein the cell culture is selected from the group consisting of an immune cell culture, a natural killer cell culture, and a stem cell.

9. The method of claim 8, wherein the immune cell culture is a chimeric antigen receptor T (CAR T) cell culture.

10. The method of claim 9, wherein the one or more molecular characteristics include T-cell activation, metabolism, exhaustion, and T-cell receptor diversity.

11. A method for assessing and optimizing cellular quality of a chimeric antigen receptor T (CAR T) cell culture, comprising:
  (a) determining one or more molecular characteristics of a pre-modified T-cell culture;
  (b) optimizing one or more parameters of an automated cell engineering system to alter the one or more molecular characteristics of the pre-modified T-cell culture;
  (c) activating the pre-modified T-cell culture with an activation reagent to produce an activated T-cell culture;
  (d) transducing the activated T-cell culture with a vector encoding a chimeric antigen receptor, to produce a CAR T-cell culture;
  (e) expanding the CAR T-cell culture;
  (f) concentrating the expanded CAR T-cell culture of (e);
  (g) harvesting the concentrated CAR-T cell culture of (f);
  (h) automatically determining via the automated cell engineering system the one or more molecular characteristics of the CAR T-cell culture during or after any one of steps (c)-(g); and
  (i) automatically optimizing one or more parameters of any one of steps (c)-(g) to alter the one or more molecular characteristics of the CAR T-cell culture based on the automatically determined one or more molecular characteristics, wherein the optimizing includes one or more of increasing or decreasing a flow rate of cell media, increasing or decreasing oxygen concentration, increasing or decreasing carbon dioxide concentration, increasing or decreasing a glucose level, increasing or decreasing a pH of cell media, and/or modifying a selection reagent used in a cell isolation procedure.

12. The method of claim 11, wherein the method produces about 100 million viable CAR T-cells.

13. The method of claim 11, wherein the T-cell culture comprises at least one accessory cell, peripheral blood mononuclear cells and/or purified T-cells.

14. The method of claim 13, wherein the accessory cell comprises a monocyte or a monocyte-derived cell and antigens for a T-cell receptor comprising CD28, CD40, CD2, CD40L and/or ICOS.

15. The method of claim 11, wherein the activation reagent comprises an antibody or a dendritic cell.

16. The method of claim 15, wherein the antibody is a soluble antibody, comprises at least one of an anti-CD3 antibody and an anti-CD28 antibody and/or is immobilized on a surface.

17. The method of claim 16, wherein the surface is a surface of a bead.

18. The method of claim 11, wherein the transducing comprises viral infection, electroporation, membrane disruption, or combinations thereof.

19. The method of claim 11, wherein the vector is a lentiviral vector or a retrovirus.

20. The method of claim 11, wherein the one or more molecular characteristics of the pre-modified T-cell culture include T-cell activation, metabolism, exhaustion, and T-cell receptor diversity, and wherein the one or more molecular characteristics of the CAR T-cell culture during or after any one of steps (c)-(g) are selected from the group consisting of a gene expression, a protein expression, an mRNA expression, and a copy number variation.

21. The method of claim 11, wherein at least 500 gene expressions are determined.

22. The method of claim 11, wherein the optimizing further includes increasing or decreasing a temperature of the CAR T-cell culture.

23. A method for assessing and optimizing cellular quality of a cell culture, comprising:
  (a) determining one or more molecular characteristics of a pre-modified cell culture;
  (b) genetically modifying the cell culture via an automated cell engineering system;
  (c) automatically determining via the automated cell engineering system the one or more molecular characteristics of the modified cell culture during and after the genetically modifying; and
  (d) automatically optimizing one or more parameters of the automated cell engineering system based on the automatically determined one or more molecular characteristics to alter the one or more molecular characteristics of the modified cell culture, wherein the optimizing includes one or more of increasing or decreasing a flow rate of cell media, increasing or decreasing oxygen concentration, increasing or decreasing carbon dioxide concentration, increasing or decrease a glucose level, increasing or decreasing a pH of cell media, and/or modifying a selection reagent used in a cell isolation procedure.

* * * * *